United States Patent
Yancopoulos et al.

(10) Patent No.: US 10,935,554 B2
(45) Date of Patent: Mar. 2, 2021

(54) DIAGNOSTIC TESTS AND METHODS FOR ASSESSING SAFETY, EFFICACY OR OUTCOME OF ALLERGEN-SPECIFIC IMMUNOTHERAPY (SIT)

(71) Applicant: REGENERON PHARMACEUTICALS, INC., Tarrytown, NY (US)

(72) Inventors: George D. Yancopoulos, Yorktown Heights, NY (US); Jamie Orengo, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 918 days.

(21) Appl. No.: 14/913,645

(22) PCT Filed: Aug. 22, 2014

(86) PCT No.: PCT/US2014/052295
§ 371 (c)(1),
(2) Date: Feb. 22, 2016

(87) PCT Pub. No.: WO2015/027154
PCT Pub. Date: Feb. 26, 2015

(65) Prior Publication Data
US 2016/0223563 A1 Aug. 4, 2016

Related U.S. Application Data

(60) Provisional application No. 61/869,214, filed on Aug. 23, 2013.

(51) Int. Cl.
*G01N 33/68* (2006.01)
*G01N 33/50* (2006.01)
*A61K 49/00* (2006.01)

(52) U.S. Cl.
CPC ..... *G01N 33/6854* (2013.01); *A61K 49/0008* (2013.01); *G01N 33/502* (2013.01); *G01N 33/5088* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,512,283 A * | 4/1996 | Byers | C07K 16/4208 424/171.1 |
| 5,670,626 A | 9/1997 | Chang et al. | |
| 6,596,541 B2 | 7/2003 | Murphy et al. | |
| 6,849,259 B2 | 2/2005 | Haurum et al. | |
| 9,079,948 B2 | 7/2015 | Orengo et al. | |
| 9,475,869 B2 | 10/2016 | Orengo et al. | |
| 2002/0009453 A1 | 1/2002 | Haurum et al. | |
| 2003/0003133 A1 | 1/2003 | Schneider | |
| 2004/0101920 A1 | 5/2004 | Radzoekewski et al. | |
| 2007/0231341 A1 | 10/2007 | McGavin et al. | |
| 2007/0280945 A1 | 12/2007 | Stevens et al. | |
| 2010/0143266 A1 | 6/2010 | Wells et al. | |
| 2010/0239599 A1 | 9/2010 | Hafner et al. | |
| 2012/0097565 A1 | 4/2012 | Dix et al. | |
| 2013/0295097 A1 | 11/2013 | Orengo et al. | |
| 2015/0299303 A1 | 10/2015 | Orengo et al. | |
| 2016/0376358 A1 | 12/2016 | Orengo et al. | |
| 2018/0305446 A1 | 10/2018 | Orengo | |

FOREIGN PATENT DOCUMENTS

| | | |
|---|---|---|
| CN | 101802015 A | 8/2010 |
| EP | 2380591 A2 | 10/2011 |
| WO | 93/13772 A1 | 7/1993 |
| WO | 1993/013772 A1 | 7/1993 |
| WO | 2005/103081 A2 | 11/2005 |
| WO | 2006/097530 A2 | 9/2006 |
| WO | 2007/065633 A1 | 6/2007 |
| WO | 2007/140505 A1 | 12/2007 |
| WO | 2007/140505 A2 | 12/2007 |
| WO | 2008/119353 A1 | 10/2008 |
| WO | 2008/145142 A1 | 12/2008 |
| WO | 2009/009061 A1 | 1/2009 |
| WO | 2008/076379 | 2/2009 |

(Continued)

OTHER PUBLICATIONS

Fisher et al. Study on passive cutaneous anaphylaxis with serum of allergic patients. The Institutue of Allergy, 256-269Roosevelt Hospital, New York City, 1956.*
Babakhin et al. 'Immunomodulatory effect of modified ragweed alergen and immune adjuvant on secondary immune responses.' J. Allergy. Clin. Immunovol. 121(s):S124 Feb. 2008. Abstract 479.*
Apicella et al.Asymmetric IgG Antibodies Induced by Different Immunotherapies in a Murine Model of Allergy . Immunological Investigations, 38:572-588, 2009.*

(Continued)

*Primary Examiner* — Nora M Rooney

(57) ABSTRACT

The present invention provides in vitro and in vivo diagnostic tests and methods for determining the safety, efficacy, or outcome of allergen-specific immunotherapy (SIT) in a patient. The present invention also provides for the measurement of allergen specific IgG and IgE in a patient tissue sample, or extract thereof, or in a biological fluid or blood sample, and determining whether the allergen-specific immunoglobulins contained in the patient sample(s), upon injection into an allergen-sensitized animal, will protect the animal following challenge with the allergen. The invention also provides methods for determining whether a patient suffering from an allergy is responsive to therapy with one or more therapeutic antibodies specific for the allergen.

5 Claims, 5 Drawing Sheets
Specification includes a Sequence Listing.

(56) References Cited

FOREIGN PATENT DOCUMENTS

| WO | 2009/023540 | | 2/2009 |
|---|---|---|---|
| WO | 2011/150008 | | 12/2011 |
| WO | 2013/166236 | A1 | 11/2013 |
| WO | 2015/027154 | A2 | 2/2015 |

OTHER PUBLICATIONS

Saloga et al. 'Development and Transfer of Immediate Cutaneous Hypersensitivity in Mice Exposed to Aerosolized Antigen.' J. Clin. Invest. 91:133-140, 1993.*

Macdonald et al., "Precise and in situ genetic humanization of 6 Mb of mouse immunoglobulin genes", Proceedings of the National Academy of Sciences of the United States of America PNAS 111(14):5147-5152 (2014).

Murphy, A. J. et al. "Mice with megabase humanization of their immunoglobulin genes generate antibodies as efficiently as normal mice", Proceedings of the National Academy of Sciences of the United States of America PNAS 111: 5153-5158 (2014).

Paterniti, M. et al., "Cat allergen-induced blood basophil reactivity in vitro predicts acute human nasal allergen challenge responses in vivo", Clinical & Experimental Allergy, Journal of the British Society for Allergy and Clinical Immunology 41: 963-969 (2011).

Scadding, G., et al., "Local and systemic effects of cat allergen nasal provocation", Clinical & Experimental Allergy, Journal of the British Society for Allergy and Clinical Immunology 45(3): 613-623 (2015).

Al-Lazikani et al., "Standard Conformations for the Canonical Structures of Immunoglobulins", J. Mol. Biol. 273: 927-948 (1997).

Anderson et al., "A comparative study of the allergens of cat urine, serum, saliva, and pelt", J. Allergy Clin,. Immunol. 76: 563-569 (1985).

Bartholome, K. et al., "Where does cat allergen 1 come from?", J. Allergy Clin,. Immunol. 76: 503-506 (1985).

Bousquet, J. et al., "Nasal challenge with pollen grans, skin-prick tests and specific IgE in patients with grass pollen allergy", Clin Allergy 17(6): 529-536 (1987).

Bradley, B.L., et al., "Eosinophils, T-lymphocytes, mast cells, neutrophils, and macrophages in bronchial biopsy specimens from atopic subjects with asthma: Comparison with biopsy specimens from atopic subjects without asthma and normal control subjects and relationship to bronchial hyperresponsiveness", J. Allergy Clin. Immunol. 88(4): 661-674 (1991).

Chapman, M.D. et al., "Monoclonal Antibodies to the Major Feline Allergen Fel d I, II. Single Step Affinity Purification of Fel d I, N-Terminal Sequence Analysis, and Development of a Sensitive Two-Site Immunoassay to Assess Fel d I Exposure", The Journal of Immunology 140(3): 812-818 (1988).

Charpin, C., et al., "Fel d I allergen distribution in cat fur and skin", J. Allergy Clin. Immunol. 88: 77-82 (1991).

Couroux, P., et al., "Fel d 1-derived synthetic peptide immunoregulatory epitopes show a long-term treatment effect in cat allergic subjects", Clinical & Experimental Allergy 45(5): 974-981 (2015).

Dabrowski, A.J. et al., "Cat skin as an important source of Fel d I allergen", J. Allergy Clin. Immunol. 86: 462-465 (1990).

Duffort, O.A. et al., "Studies on the biochemical structure of the major cat allergen Felis domesticus 1", Molecular Immunoloty 28(4/5): 301-309 (1991).

Durham, S.R. et al., "Long-term clinical efficacy of grass-pollen immunotherapy", The New England Journal of Medicine 341(7): 468-475.

Durham, S.R. et al., "Treatment effect of sublingual immunotherapy tablets and pharmacotherapies for seasonal and perennial allergic rhinitis: Pooled analyses", J. Allergy Clin. Immunol. 138(4): 1-12.

Flicker, S. et al., "Passive Immunization with Allergen-Specific Antibodies", Current Topics in Microbiology and Immunology 352: 141-159 (2011).

Griffith, I.J. et al., Expression and genomic structure of the genes encoding Fdl, the major allergen from the domestic cat (Polymerase chain reaction; allergy; Felis domesticus; alternate splicing; differential tissue-specific expression), Gene 113: 263-268 (1992).

Hansen, I. et al., "Mediators of inflammation in the early and the late phase of allergic rhinitis", Current Opinion in Allergy and Clinical Immunology 4(3): 159-163 (2004).

Hedlin, G. et al., "Immunotherapy with cat- and dog-dander extracts; V. Effects of 3 years of treatment", J. Allergy Clin. Immunol. 87: 955-964 (1991).

Ichikawa, K. et al., "Molecular cloning, expression and modelling of cat allergen, cystatin (Fel d 3), a cysteine protease inhibitor", Clinical and Experimental Allergy, 31: 1279-1286 (2001).

Junghans, R.P, et al., "Anti-Tac-H, a Hummanized Antibody to the Interleukin 2 Receptor with New Features for Immunotherapy in Malignant and Immune Disorders", Cancer Research 50: 1945-1502 (1990).

Kabat, E.A et al., "Sequences of Proteins of Immunological Interest", Fifth Edition, National Institutes of Health, Bethesda, Md. (1991).

Kaiser, L. et al., "The Crystal Structure of the Major Cat Allergen Fel d 1, a Member of the Secretoglobin Family", The Journal of Biological Chemistry, 278(39): 37730-37735 (2003).

Kaiser, L. et al., "Structural Characterization of the Tetrameric form of the Major Cat Allergen Fel d 1", J. Mol. Biol. 370: 714-727 (2007).

Kazane, S.A. et al., "Self-Assembled Antibody Multimers through Peptide Nucleic Acid Conjugation", Journal of the American Chemical Society, 135: 340-346 (2013).

Klein, C. et al., "Progress in overcoming the chain association issue in bispecific heterodimeric IgG antibodies", mAbs 4:6; 653-663 (2012).

Klug, J. et al., "Uteroglobin/Clara Cell 10-kDa Family of Proteins: Nomenclature Committee Report", Annals New York Academy of Sciences 923:348-354 (2000).

Kristensen, A.K. et al., "Determination of Isoforms, N-Linked Glycan Structure and Disulfide Bond Linkages of the Major Cat Allergen Fel d 1 by a Mass Spectrometric Approach", Boil. Chem 378: 899-908 (1997).

Larché, M. et al., "Immunological mechanisms of allergen-specific immunotherapy", Immunology 6(10): 761-771 (2006).

Lau, S. et al., "Early exposure to house-dust mite and cat allergens and development of childhood asthma: a cohort study", The Lancet, 356: 1392-1397 (2000).

Leitermann, K. et al., "Cat allergen 1: Biochemical, antigenic, and allergenic properties", J. Allergy Clin. Immunol. 74: 147-153 (1984).

Lilja, G. et al., "Immunotherapy with cat- and dog-dander extracts; V. Effects of 2 years of treatment", J. Allergy Clin. Immunol. 83: 37-44 (1989).

Liu, Y., et al. "An essential role for RasGRP1 in mast cell function and IgE-mediated allergic response", The Journal of Experimental Medicine 204(1): 93-103 (2007).

Loyd, V.A. "The Art, Science, and Technology of Pharmaceutical Compounding", American Pharmaceutical Association, 1998.

Løwenstein, H. et al., "Identification and Clinical Significance of Allergenic Molecules of Cat Origin", Allergy 40: 430-441 (1985).

Martin, A.C.R et al., "Modeling antibody hypervariable loops: A combined algorithm", Proc. Natl. Acad. Sci. USA 86: 9268-9272 (1989).

Mata, P. et al., "Fel d I allergen: skin and or saliva?", Annals of Allergy 69(4): 321-322 (1992).

Morgenstern, J.P. et al., "Amino acid sequence of Fel dI, the major allergen of the domestic cat: Protein sequence analysis and cDNA cloning", Proc. Natl. Acad. Sci. USA 88: 9690-9694 (1991).

Nicholson, G.C. et al., "The effects of an anti-IL-13 mAb on cytokine levels and nasal symptoms following nasal allergen challenge", J. Allerg Clin. Immunol. 128: 800-807 (2011).

Noon, L. "Prophylactic Inoculation Against Hay Fever", The Lancet 1: 1572-1573 (1911).

Norman, P.S. et al., "Treatment of Cat Allergy with T-cell Reactive Peptide", Am. J. Respir. Crit. Care Med. 154: 1623-1628 (1996).

Ocmant, A. et al., "Flow cytometry for basophil activation markers: The measurement of CD203c up-regulation is as reliable as CD63 expression in the diagnosis of cat allergy", Journal of Immunological Methods 320: 40-48 (2007).

(56) References Cited

OTHER PUBLICATIONS

Oldfield, W.L.G. et al., "Effect of T-cell peptides derived from Fel d 1 on allergic reactions and cytokine production in patients sensitive to cats: a randomised controlled trial", The Lancet 360: 47-53 (2002).
Patel, D. et al., "Fel d 1-derived peptide antigen desensitization shows a persistent treatment effect 1 year after the start of dosing: A randomized, placebo-controlled study", J. Allergy Clin. Immunol. 131(1): 162-168 (2016).
Platts-Mills, T.A.E. et al., "Indoor allergens and asthma: Report of the Third International Workshop", J. Allergy Clin. Immunol 100: S2-S24 (1997).
Powell, M.F. et al., "Compendium of Excipients for Parenteral Formulations", PDA, J. Pharm. Sci. Technol 52: 238-311 (1998).
Reismann, R.E. "Natural history of insect sting allergy: Relationship of severity of symptoms of initial sting anaphylaxis to re-sting reactions", Journal of Allergy and Clinical Immunology 90 (3 Pt 1):335-339 (1992).
Spertini, F. et al., "Efficacy of 2 months of allergen-specific immunotherapy with Bet v 1-derived contiguous overlapping peptides in patients with allergic rhinoconjunctivitis: Results of a phase IIb study", J. Allergy Clin. Immunol. 138: 162-168 (2016).
Sturm, E.M. et al., "CD203c-Based Basophil Activation Test in Allergy Diagnosis: Characteristics and Differences to CD63 Upregulation", Cytometry Part B (Clinical Cytometry) 78B: 308-318 (2010).
P. A. Würtzen et al.:"A double-blind placebo-controlled birch allergy vaccination study II: correlation between inhibition of IgE binding, histamine release and facilitated allergen presentation"; Clinical and Experimental Allergy, vol. 38, No. 8, Aug. 1, 2008, pp. 1290-1301.
Christian Möbs et al.: "Birch pollen immunotherapy results in long-term loss of Bet v 1-specific TH2 responses, transient TRI activation, and synthesis of IgE-blocking antibodies"; Journal of Allergy and Clinical Immunology,vol. 130, No. 5, Nov. 1, 2012, pp. 1108-1116.
A. Babakhin et al.: "Experimental desensitisation using a modified allergen adsorbed onto a synthetic Immunomodulator in a murine model of allergic asthma"; Allergy,vol . 62, No. Suppl . 83, Jun. 13, 2007, p. 252.
A. Babakhin et al.: "Allergen-specific Immunotherapy Using a Highly Modified Allergen and the Immunomodulator Polyoxidonium in a Murine Model of Allergic Asthma"; Journal of Allergy and Clinical Immunology, Elsevi Er, Amsterdam, NL, vol. 119, No. I, Jan. 1, 2007, p. S59.
Katarzyna Niespodziana et al.: "A hypoallergenic cat vaccine based on Fel d 1-derived peptides fused to hepatitis B PreS"; Journal of Allergy and Clinical Immunology, vol. 127, No. 6, Jun. 1, 2011, pp. 1562-1570.
Teresa E. Twaroch et al. : "Carrier-bound, nonallergenic Ole e 1 peptides for vaccination against olive pollen allergy"; Journal of Allergy and Clinical Immunology, vol. 128, No. I , Jul. 1, 2011, pp. 178-184.
Agata Giallongo et al: "IgE and IgG antibodies compete for antigenic determinants of Parietaria officinalis allergen"; Molecular Immunology, Pergamon, GB, vol. 17, No. 8, Aug. 1, 1980, pp. 1019-1024.
International Search Report for PCT/US2014/052295, dated Mar. 13, 2015, with Written Opinion.
G. Hedlin et al.: "Immunotherapy with cat- and dog- dander extracts"; J. Allergy Clin. Immunol. (1991), vol. 87, No. 5, pp. 955-964.
G. Hedlin et al.: "Immunotherapy with cat- and dog- danger extract"; J. Allergy Clin. Immunol. (1986), vol. 77, No. 3, pp. 488-496.
L. Cox et al.: "Allergen Immunotherapy: A practice parameter second update"; J. Allergy Clin. Immunol. (2007), vol. 120, No. 3, pp. S25-S85.
B. Bradley et al.: "Eosinophils, T-lymphocytes, mast cells, neutrophils, and macrophages in bronchial biopsy specimens from atopic subjects with asthma: Comparison with biopsy specimens from atopic subjects without asthma and normal control subjects and relationship to bronchial hyperresponsiveness"; J. Allergy Clin. Immunol. (1991), vol. 88, No. 4, pp. 661-674.
O. A. Duffort et al.: "Studies on the Biochemical Structure of the Major Cat Allergen *Felis domesticus* I"; Molecular Immunology (1991), vol, 28, No. 4/5, pp. 301-309.
A. K. Kristensen et al.: "Determination of Isoforms, N-Linked Glycan Structure and Disulfide Bond Linkages of the Major Cat Allergen Fel d1 a Mass Spectrometric Approach"; Biol. Chem. (1997), vol. 378, pp. 899-908.
L. Kaiser et al.: "The Crystal Structure of the Major Cat Allergen Fel d 1, a Member of the Secretoglobin Family"; The Journal of Biological Chemistry (2003), vol. 278, No. 39, pp. 37730-37735.
E. Padlan et al.: "Identification of specificity-determining residues in antibodies"; The FASEB Journal (1995), vol. 9, pp. 133-139.
F. Vajdos et al.: "Comprehensive Functional Maps of the Antigen-binding Site of an Anti-ErbB2 Antibody Obtained with Shotgun Scanning Mutagenesis"; J. Mol. Biol. (2002), vol. 320, pp. 415-428.
L. Taylor et al.: "A transgenic mouse that expresses a diversity of human sequence heavy and light chain immunoglobulins"; Nucleic Acids Research (1992), vol. 20, No. 23, pp. 6287-6295.
M. Shamji et al.: "The IgE-facilitated allergen binding (FAB) assay: validation of a novel flow-cytometric based method for the detection of inhibitory antibody responses"; J Immunol Methods (2006), vol. 317(1-2), pp. 71-79.
M. Powell et al.: "Compendium of Excipients for Parenteral Formulations"; PDA Journal of Pharmaceutical Science & Technology (1998), vol. 52, No. 5, pp. 238-311.
G. Wu et al.: "Receptor-mediated in Vitro Gene Transformation by a Soluble DNA Carrier System"; The Journal of Biological Chemistry (1987), vol. 262, No. 2, pp. 4429-4432.
J. Goodson: "Chapter 6: Dental Applications—Medical Applications of Controlled Release", vol. II, Applications and Evaluation (1984), vol. 2, pp. 115-138.
R. Langer: "New Methods of Drug Delivery"; Science (1990), vol. 249, pp. 1527-1533.
R. Cooke et al: "Serological Evidence of Immunity With Coexisting Sensitization in a Type of Human Allergy (Hay Fever)"; Immunity and Sensitization in Allergy (1935), pp. 733-750.
M. Chapman et al.: "Monoclonal Antibodies to the Major Feline Allergen Fel d I"; The Journal of Immunology (1988), vol. 140, No. 3, pp. 812-818.
M. Kulis et al.: "Single-tree nut immunotherapy attenuates allergic reactions in mice with hypersensitivity to multiple tree nuts"; J. Allergy Clin. Immunol. (2011), vol. 127(1), pp. 81-88.
G. Evan et al.: "Isolation of Monoclonal Antibodies Specific for Human c-myc Proto-Oncogene Product"; Molecular and Cellular Biology (1985), vol. 5, No. 12, pp. 3610-3616.
Mariuzza, R.A. et al. 'The Structural Basis of Antigen-Antibody Recognition' Annu. Rev. Biophys. Biphys. Chem. 16:139-159 (1987).
Rudikoff, S. et al. "Single Amino Acid Substitution Altering Antigen-Binding Specificity" Proc. Natl. Acad. Sci. USA (PNAS) 79: 1979-1983 (1982).
Rader, C. et al., "A phage display approach for rapid antibody humanization: Designed combinatorial V gene libraries", Proc. Natl. Acad. Sci. USA (PNAS) 95: 8910-8915 (1998).
PCT Invitation to Pay Fees with respect to PCT/US2013/039192, dated Jul. 30, 2013.
Cady et al. (2010) "IgG antibodies produced during subcutaneous allergen immunotherapy mediate inhibition of basophil activation via a mechanism involving both FcgammaRIIA and FcgammaRIIB" Immunol. Letters, 130 (1-2):57-65.
Chapman et al. (1988) "Monoclonal Antibodies to the Major Feline Allergen Fel d I. II. Single step affinity purification of Fel d I, N-terminal sequence analysis, and development of a sensitive two-site immunoassay to assess Fel d I exposure" The Journal of Immunology, 140(3):812-818.
Davies et al. (1996) "Affinity improvement of single antibody VH domains: residues in all three hypervariable regions affect antigen binding" Immunotechnology, 2(3):169-179.
De Groot et al. (1988) "Monoclonal antibodies to the major feline allergen Fel d I. I. Serologic and biologic activity of affinity-purified Fel d I and of Fel d I-deplated extract", J. Allergy Clin. Immunol., 82 (5):778-786.

(56) References Cited

OTHER PUBLICATIONS

Holt et al. (2003) "Domain antibodies: proteins for therapy" Trends in Biotechnology, 21(11):484-490.
Martínez-Gómez et al. (2008) "Targeting the MHC class II pathway of antigen presentation enhances immunogenicity and safety of allergen immunotherapy" Allergy, 64(1):172-178.
Ormstad et al. (2003) "The effect of endotoxin on the production of IgE, IgG1 and IgG2a antibodies against the cat allergen Fel d 1in mice" Toxicology, 188(2-3):309-318.
Saarne et al. (2011) "Treatment with a Fel d 1 hypoallergen reduces allergic responses in a mouse model for cat allergy" Allergy, 66(2):255-263.
Senti et al. (2012) "Intralymphatic immunotherapy for cat allergy induces tolerance after only 3 injections" J. Allergy Clin. Immunol., 129(5):1290-1296.
Uermösi et al. (2010) "Mechanisms of allergen-specific desensitization" J. Allergy Clin. Immunol., 125:375-383.
Van Ree et al. (1999) "Purified natural and recombinant Fel d 1 and cat albumin in in vitro diagnostics for cat allergy" J. Allergy Clin. Immunol., 104(6): 1223-1230.
Van Milligen et al. (1993) "Calculation of the affinity constant KASS for solid phase antigen—A model system using monoclonal antibodies against the cat allergen Fel d I" Journal of Immunological Methods, 162(2):165-173.
Carter (2006) "Potent Antibody Therapeutics by Design" Journal of Immunology 6:343-357.
International Search Report and Written Opinion for PCT/US2013/039192, dated Sep. 19, 2013.
Wark et al. (2006) "Latest Technologies for the Enhancement of Antibody Affinity" Advanced Drug Delivery Reviews 58(5-6):657-670.
Al-Lazikani et al. (1997) "Standard Conformations for the Canonical Structures of Immunoglobulins", J. Mol. Biol., 273:927-948.
Altschul et al. (1990) "Basic Local Alignment Search Tool", J. Mol. Biol., 215:403-410.
Altschul et al. (1997) "Gapped BLAST and PSI-BLAST: a new generation of protein database search programs", Nucleic Acids Research, 25(17):3389-3402.
Ehring (1999) "Hydrogen Exchange/Electrospray Ionization Mass Spectrometry Studies of Structural Features of Proteins and Protein/Protein Interations", Analytical Biochenistry, 267:252-259.
Engen et al. (2001) "A powerful new approach that goes", Analytical Chemistry:257 A-265 A.
Gonnet et al. (1992) "Exhaustive Matching of the Entire Protein Sequence Database", Science, 256:1443-1445.
Junghans et al. (1990) "Anti-Tac-H, a Humanized Antibody to the Interleukin 2 Receptor with New Features for Immunotherapy in Malignant and Immune Disorders", Cancer Research 50:1495-1502.
Kufer et al. (2004) "A revival of bispecific antibodies", TRENDS in Biotechnology, 22(5):238-244.
Langer (1990) "New Methods of Drug Delivery", Articles:1527-1533.
Martin et al. (1989) "Modeling antibody hypervariable loops: A combined algorithm", Proc. Natl. Acad. Sci. USA, 86:9268-9272.
Padlan et al. (1995) "Identification of specificity-determining residues in antibodies", Research Communications, 9:133-139.
Pearson (1994) "Using the FASTA Program to Search Protein and DNA Sequence Databases", Methods in Molecular Biology, 24:307-331.
Reddy et al. (2000) "Elimination of Fc Receptor-Dependent Effector Functions of a Modified IgG4 Monoclonal Antibody to Human CD4", The Journal of Immunology, 164:1925-1933.
Reineke (2004) "Antibody Epitope Mapping Using Arrays of Synthetic Peptides", Methods in Molecular Biology, Antibody Engineering: Methods and Protocols, 248:443-463.
Shields et al. (2002) "Lack of Fucose on Human IgG1 N-Linked Oligosaccharide Improves Binding to Human FcgammaRIII and Antibody-dependent Cellular Toxicity", The Journal of Biological Chemistry, 277 (30):26733-26740.
Tutt et al. (1991) "Trispecific F(ab')3 Derivatives that Use Cooperative Signaling via the TCR/CD3 Complex and CD2 to Activate and Redirect Resting Cytotoxic T Cells", The Journal of Immunology, 147(1):60-69.
Vajdos (2002) "Comprehensive Functional Maps of the Antigen-binding Site of an Anti-ErbB2 Antibody Obtained with Shotgun Scanning Mutagenesis", J. Mol. Biol., 320:415-428.
Wu et al. (1987) "Receptor-mediated in Vitro Gene Transformation by a Soluble DNA Carrier System", The Journal of Biological Chemistry, 262(10):4429-4432.
T.S. Dodev et al. (2015) "Inhibition of allergen-dependent IgE activity by antibodies of the same specificity but different class", Allergy, 70(6):720-724.
R.T. Strait (2006) "IgG-blocking antibodies inhibit IgE-mediated anaphylaxis in vivo through both antigen interception in vivo through both antigen interception and FcRIIb cross-linking", Journal of Clinical Investigation, 116 (3):833-841.
International Search Report for PCT/US2017/066838, dated Apr. 23, 2018.
Hochleitner, E.O and Tomer, K.B et al., "Characterization of a discontinuous epitope of the human Immunodeficiency virus (HIV) core protein p24 by epitope excision and differential chemical modification followed by mass spectrometric peptide mapping analysis", Protein Science 9:487-496 (2000).
Valenta, R. et al., "Vaccine development for allergen-specific immunotherapy based on recombinant allergens and synthetic allergen peptides: Lessons from the past and novel mechanisms of action for the future", J. Allergy & Clin. Immunol. 137(2): 375-378 (1992).
Van Milligen, F.J. et al., "Presence of *Felis domesticus* Allergen I in the Cat's Salivary and Lacrimal Glands", Int. Arch. Allergy Appl. Immunol. 92: 375-378 (1992).
Van Ree, R. et al., "Purified natural and recombinant Fel d 1 and cat albumin in in vitro diagnostics for cat allergy", J. Allergy Clin. lmmunol. 104: 1223-1230 (1999).
Worm, M. et al., "Development and preliminary clinical evaluation of a peptide immunotherapy vaccine for cat allergy", Journal of Allergy and Clinical Immunology 127(1): 89-97 (2011).
Wo, W. et al., "An integrated analysis of the efficacy of fluticasone furoate nasal spray versus placebo on the nasal symptoms of perennial allergic rhinitis", Allergy Asthma Proc May-June 34(3): 283-291 (2013).
Zhu, M. et al., "The Role of Ras Guanine Nucleotide Releasing Protein 4 in FceRI-mediated Signaling, Mast Cell Function, and T Cell Development", The Journal of Biological Chemistry 287(11): 8135-8143 (2012).
European Extended Search Report in Application 19178233.3, dated Jul. 26, 2019, 10 pages.
PCT International Search Report and Written Opinion in International Application PCT/US2017/066838, dated Jan. 23, 2018, 28 pages.
Zhu, et al., "A chimeric human-cat fusion protein blocks cat-induced allergy", Nat. Med., vol. 11, pp. 446-449, 2005.
Mueller, Geoffrey et al., "Structural analysis of recent allergen-antibody complexes and future directions", Current Allergy and Asthma Reports, Current Science, US, vol. 19, No. 3, Feb. 28, 2019, pp. 1-10.
Orengo, J. M. et al., "Treating cat allergy with monoclonal IgG antibodies that bind allergen and prevent IgE engagement", Nature Communications, vol. 9, No. 1, Dec. 12, 2018, 15 pgs.
Zhang, Ke et al., "Inhibition of allergen-specific IgE reactivity by a human IgFcgamma-Fcepsilon bifunctional fusion protein", Journal of Allergy and Clinical Immunology, vol. 114, No. 2, Aug. 1, 2004, pp. 321-327.

\* cited by examiner

A

B

SEQUENCE LISTING

```
<160> NUMBER OF SEQ ID NOS: 53

<210> SEQ ID NO 1
<211> LENGTH: 357
<212> TYPE: DNA
<213> ORGANISM: Artificial Sequence
<220> FEATURE:
<223> OTHER INFORMATION: Synthetic

<400> SEQUENCE: 1
gaggtgcagc tggtggagtc tgggggaggc ctggtcaagc ctgggggtc cctgagactc      60 tcctgtgcag cctctggatt caccttcaga aactataaca taaactgggt ccgccaggct     120
ccagggaagg gctggagtg gtctcactc atcagtggta gtagtagtta catatattac       180
gcagactcag tgaagggccg attcaccgtc tccagagaca acgccaagaa ctcactgtat     240
ctgcaaatga acagcctgag agccgaggac acggctgtgt attactgtgc gaggcggaca     300
ttaagctact acgttatgga cgtctggggc caagggacca cggtcaccgt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Arg Asn Tyr
            20                  25                  30

Asn Ile Asn Trp Val Arg Gln Ala Pro Gly Lys Gly Leu Glu Trp Val
        35                  40                  45

Ser Leu Ile Ser Gly Ser Ser Ser Tyr Ile Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Leu Ser Tyr Tyr Val Met Asp Val Trp Gly Gln Gly
            100                 105                 110

Thr Thr Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagaaacta taac                                              24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Arg Asn Tyr Asn
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atcagtggta gtagtagtta cata                                              24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Gly Ser Ser Ser Tyr Ile
1               5

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gcgaggcgga cattaagcta ctacgttatg gacgtc                           36

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Ala Arg Arg Thr Leu Ser Tyr Tyr Val Met Asp Val
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccagg tgacccagtc tccatccccc ctgtctgcat ctgtaggaga cagagtcacc    60
atcacttgcc gggcgagtca gggcattagc aattatttag cctggtatca gcagaaacca   120
gggagagttc ctcagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg ccccgtacac ttttggccag   300
gggaccaagc tggagatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Val Thr Gln Ser Pro Ser Pro Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Arg Val Pro Gln Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagggcatta gcaattat                                                  18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Gly Ile Ser Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                             9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caaaagtata acagtgcccc gtacact                                        27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Lys Tyr Asn Ser Ala Pro Tyr Thr
1               5

<210> SEQ ID NO 17
<211> LENGTH: 345
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggc ttggtacagc ctggggggtc cctgagactc    60
tcctgtgcag cctctggatt cacctttagc agttatgcca tgagctgggt ccgccaggct   120
```

```
ccagggaagg ggctggagtg ggtctcagct attagtggtc gtggttataa cgcagactac    180
gcagactccg tgaagggccg gttcaccatc tccagggaca attccaagaa cacgctgtat    240
ctgcaaatga acagcctgag agccgaagac acggccgtat attactgtgc gaaattggaa    300
tactttgact actggggcca gggaaccctg gtcactgtct cctca                    345
```

<210> SEQ ID NO 18
<211> LENGTH: 115
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Tyr Asn Ala Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Glu Tyr Phe Asp Tyr Trp Gly Gln Gly Thr Leu Val Thr
            100                 105                 110

Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggattcacct ttagcagtta tgcc                                            24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Phe Thr Phe Ser Ser Tyr Ala
1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21

```
attagtggtc gtggttataa cgca                                            24
```

```
<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Gly Arg Gly Tyr Asn Ala
1               5

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
gcgaaattgg aatactttga ctac                                          24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Ala Lys Leu Glu Tyr Phe Asp Tyr
1               5

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagat tcactctcac catcagcag cctgaggcct      240 gaagattttg caacttatta ctgccaacag tataatagtt accctctgac tttcggcgga     300
gggaccaagg tggagatcaa a                                               321

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

Tyr Lys Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagagtatta gtagctgg                                              18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Ser Ile Ser Ser Trp
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 aaggcgtct                                                         9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Lys Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caacagtata atagttaccc tctgact                                    27

<210> SEQ ID NO 32
<211> LENGTH: 9
<212> TYPE: PRT

<213> ORGANISM: Artificial Sequence
<220> FEATURE:
<223> OTHER INFORMATION: Synthetic

<400> SEQUENCE: 32

Gln Gln Tyr Asn Ser Tyr Pro Leu Thr
1               5

<210> SEQ ID NO 33
<211> LENGTH: 70
<212> TYPE: PRT
<213> ORGANISM: Artificial Sequence
<220> FEATURE:
<223> OTHER INFORMATION: Synthetic

<400> SEQUENCE: 33

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
                20                  25                  30

Val Val Leu Glu Asn Ala Arg Ile Leu Lys Asn Cys Val Asp Ala Lys
            35                  40                  45

Met Thr Glu Glu Asp Lys Glu Asn Ala Leu Ser Leu Leu Asp Lys Ile
        50                  55                  60

Tyr Thr Ser Pro Leu Cys
65                  70

<210> SEQ ID NO 34
<211> LENGTH: 92
<212> TYPE: PRT
<213> ORGANISM: Artificial Sequence
<220> FEATURE:
<223> OTHER INFORMATION: Synthetic

<400> SEQUENCE: 34

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
                20                  25                  30

Asn Ala Thr Glu Pro Glu Arg Thr Ala Met Lys Lys Ile Gln Asp Cys
            35                  40                  45

Tyr Val Glu Asn Gly Leu Ile Ser Arg Val Leu Asp Gly Leu Val Met
        50                  55                  60

Thr Thr Ile Ser Ser Ser Lys Asp Cys Met Gly Glu Ala Val Gln Asn
65                  70                  75                  80

Thr Val Glu Asp Leu Lys Leu Asn Thr Leu Gly Arg
                85                  90

<210> SEQ ID NO 35
<211> LENGTH: 360
<212> TYPE: DNA
<213> ORGANISM: Artificial Sequence
<220> FEATURE:
<223> OTHER INFORMATION: synthetic

<400> SEQUENCE: 35
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattggatat atctattaca gtgggagaac caactacaac    180
ccctccctca agagtcgagt caccatatca gtggacacgt ccaagaacca gttctccctg    240
aaactgagct ctgtgaccgc cgcagacacg gccatttatt actgtgcgag acatcgtgta 300
actagaactg cggactcctt tgactactgg ggccagggaa ccctggtcac cgtctcctca 360

<210> SEQ ID NO 36
<211> LENGTH: 120
<212> TYPE: PRT
<213> ORGANISM: Artificial Sequence
<220> FEATURE:
<223> OTHER INFORMATION: synthetic

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Arg Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg His Arg Val Thr Arg Thr Ala Asp Ser Phe Asp Tyr Trp Gly Gln
            100                 105                 110

Gly Thr Leu Val Thr Val Ser Ser
        115                 120

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
ggtggctcca tcagtagtta ctac                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Gly Gly Ser Ile Ser Ser Tyr Tyr
1               5

<210> SEQ ID NO 39
<211> LENGTH: 21
<212> TYPE: DNA
<213> ORGANISM: Artificial Sequence
<220> FEATURE:
<223> OTHER INFORMATION: synthetic

<400> SEQUENCE: 39
atctattaca gtgggagaac c                                             21

<210> SEQ ID NO 40
<211> LENGTH: 7

```
<212> TYPE: PRT
<213> ORGANISM: Artificial Sequence
<220> FEATURE:
<223> OTHER INFORMATION: synthetic

<400> SEQUENCE: 40

Ile Tyr Tyr Ser Gly Arg Thr
1               5

<210> SEQ ID NO 41
<211> LENGTH: 42
<212> TYPE: DNA
<213> ORGANISM: Artificial Sequence
<220> FEATURE:
<223> OTHER INFORMATION: synthetic

<400> SEQUENCE: 41
gcgagacatc gtgtaactag aactgcggac tcctttgact ac                          42

<210> SEQ ID NO 42
<211> LENGTH: 14
<212> TYPE: PRT
<213> ORGANISM: Artificial Sequence
<220> FEATURE:
<223> OTHER INFORMATION: synthetic

<400> SEQUENCE: 42

Ala Arg His Arg Val Thr Arg Thr Ala Asp Ser Phe Asp Tyr
1               5                   10

<210> SEQ ID NO 43
<211> LENGTH: 321
<212> TYPE: DNA
<213> ORGANISM: Artificial Sequence
<220> FEATURE:
<223> OTHER INFORMATION: synthetic

<400> SEQUENCE: 43
gacatccaga tgacccagtc tccatcctcc ctgtctgcat ctgtaggaga cagagtcacc        60
atcacttgcc aggcgagtca ggacattaac aactatttaa attggtatca gcagaaaaca       120
gggaaagccc ctaagttcct gatctacgat gcatccaatt tggaaacagg ggtctcatca       180
aggttcagtg gaagtggatc tgggacagat tttactttca ccatcagcag cctgcagcct       240
gaagatgttg aacatatta ctgtcaccag tatggtgatc tcccgtacac ttttggccag       300
gggaccaagc tggagatcaa a                                                 321

<210> SEQ ID NO 44
<211> LENGTH: 107
<212> TYPE: PRT
<213> ORGANISM: Artificial Sequence
<220> FEATURE:
<223> OTHER INFORMATION: synthetic

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Thr Gly Lys Ala Pro Lys Phe Leu Ile
        35                  40                  45

Tyr Asp Ala Ser Asn Leu Glu Thr Gly Val Ser Ser Arg Phe Ser Gly
    50                  55                  60
```

Ser Gly Ser Gly Thr Asp Phe Thr Phe Thr Ile Ser Ser Leu Gln Pro
65                  70                  75                  80

Glu Asp Val Gly Thr Tyr Tyr Cys His Gln Tyr Gly Asp Leu Pro Tyr
                85                  90                  95

Thr Phe Gly Gln Gly Thr Lys Leu Glu Ile Lys
            100                 105

<210> SEQ ID NO 45
<211> LENGTH: 18
<212> TYPE: DNA
<213> ORGANISM: Artificial Sequence
<220> FEATURE:
<223> OTHER INFORMATION: synthetic

<400> SEQUENCE: 45
caggacatta acaactat                                                        18

<210> SEQ ID NO 46
<211> LENGTH: 6
<212> TYPE: PRT
<213> ORGANISM: Artificial Sequence
<220> FEATURE:
<223> OTHER INFORMATION: synthetic

<400> SEQUENCE: 46

Gln Asp Ile Asn Asn Tyr
1               5

<210> SEQ ID NO 47
<211> LENGTH: 9
<212> TYPE: DNA
<213> ORGANISM: Artificial Sequence
<220> FEATURE:
<223> OTHER INFORMATION: synthetic

<400> SEQUENCE: 47 gatgcatcc                                                                   9

<210> SEQ ID NO 48
<211> LENGTH: 3
<212> TYPE: PRT
<213> ORGANISM: Artificial Sequence
<220> FEATURE:
<223> OTHER INFORMATION: synthetic

<400> SEQUENCE: 48

Asp Ala Ser
1

<210> SEQ ID NO 49
<211> LENGTH: 27
<212> TYPE: DNA
<213> ORGANISM: Artificial Sequence
<220> FEATURE:
<223> OTHER INFORMATION: synthetic

<400> SEQUENCE: 49
caccagtatg gtgatctccc gtacact                                              27

<210> SEQ ID NO 50
<211> LENGTH: 9
<212> TYPE: PRT
<213> ORGANISM: Artificial Sequence
<220> FEATURE:
<223> OTHER INFORMATION: synthetic

<400> SEQUENCE: 50

His Gln Tyr Gly Asp Leu Pro Tyr Thr
1               5

<210> SEQ ID NO 51
<211> LENGTH: 413
<212> TYPE: PRT
<213> ORGANISM: Artificial Sequence
<220> FEATURE:
<223> OTHER INFORMATION: hFceR1a-mFc

<400> SEQUENCE: 51

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Glu Pro Arg Gly Pro Thr Ile Lys Pro Cys Pro Pro
            180                 185                 190

Cys Lys Cys Pro Ala Pro Asn Leu Leu Gly Gly Pro Ser Val Phe Ile
        195                 200                 205

Phe Pro Pro Lys Ile Lys Asp Val Leu Met Ile Ser Leu Ser Pro Ile
210                 215                 220

Val Thr Cys Val Val Val Asp Val Ser Glu Asp Asp Pro Asp Val Gln
225                 230                 235                 240

Ile Ser Trp Phe Val Asn Asn Val Glu Val His Thr Ala Gln Thr Gln
                245                 250                 255

Thr His Arg Glu Asp Tyr Asn Ser Thr Leu Arg Val Val Ser Ala Leu
            260                 265                 270

Pro Ile Gln His Gln Asp Trp Met Ser Gly Lys Glu Phe Lys Cys Lys
        275                 280                 285

Val Asn Asn Lys Asp Leu Pro Ala Pro Ile Glu Arg Thr Ile Ser Lys
290                 295                 300

Pro Lys Gly Ser Val Arg Ala Pro Gln Val Tyr Val Leu Pro Pro Pro
305                 310                 315                 320

Glu Glu Glu Met Thr Lys Lys Gln Val Thr Leu Thr Cys Met Val Thr
                325                 330                 335

Asp Phe Met Pro Glu Asp Ile Tyr Val Glu Trp Thr Asn Asn Gly Lys

```
                340                 345                 350
Thr Glu Leu Asn Tyr Lys Asn Thr Glu Pro Val Leu Asp Ser Asp Gly
                355                 360                 365
Ser Tyr Phe Met Tyr Ser Lys Leu Arg Val Glu Lys Lys Asn Trp Val
            370                 375                 380
Glu Arg Asn Ser Tyr Ser Cys Ser Val Val His Glu Gly Leu His Asn
385                 390                 395                 400
His His Thr Thr Lys Ser Phe Ser Arg Thr Pro Gly Lys
                405                 410

<210> SEQ ID NO 52
<211> LENGTH: 199
<212> TYPE: PRT
<213> ORGANISM: Artificial Sequence
<220> FEATURE:
<223> OTHER INFORMATION: Feld1-mmH

<400> SEQUENCE: 52

Val Lys Met Ala Glu Thr Cys Pro Ile Phe Tyr Asp Val Phe Phe Ala
1               5                   10                  15
Val Ala Asn Gly Asn Glu Leu Leu Leu Asp Leu Ser Leu Thr Lys Val
                20                  25                  30
Asn Ala Thr Glu Pro Glu Arg Thr Ala Met Lys Lys Ile Gln Asp Cys
            35                  40                  45
Tyr Val Glu Asn Gly Leu Ile Ser Arg Val Leu Asp Gly Leu Val Met
        50                  55                  60
Thr Thr Ile Ser Ser Lys Asp Cys Met Gly Glu Ala Val Gln Asn
65                  70                  75                  80
Thr Val Glu Asp Leu Lys Leu Asn Thr Leu Gly Arg Glu Ile Cys Pro
                85                  90                  95
Ala Val Lys Arg Gly Val Asp Leu Phe Leu Thr Gly Thr Pro Asp Glu
            100                 105                 110
Tyr Val Glu Gln Val Ala Gln Tyr Lys Ala Leu Pro Val Val Leu Glu
        115                 120                 125
Asn Ala Arg Ile Leu Lys Asn Cys Val Asp Ala Lys Met Thr Glu Glu
130                 135                 140
Asp Lys Glu Asn Ala Leu Ser Leu Leu Asp Lys Ile Tyr Thr Ser Pro
145                 150                 155                 160
Leu Cys Gly Pro Gly Gly Glu Gln Lys Leu Ile Ser Glu Glu Asp Leu
                165                 170                 175
Gly Gly Glu Gln Lys Leu Ile Ser Glu Glu Asp Leu Ser Gly His His
            180                 185                 190
His His His His Ser Ser Gly
        195

<210> SEQ ID NO 53
<211> LENGTH: 398
<212> TYPE: PRT
<213> ORGANISM: Artificial Sequence
<220> FEATURE:
<223> OTHER INFORMATION: Feld1-mFc

<400> SEQUENCE: 53

Val Lys Met Ala Glu Thr Cys Pro Ile Phe Tyr Asp Val Phe Phe Ala
1               5                   10                  15
Val Ala Asn Gly Asn Glu Leu Leu Leu Asp Leu Ser Leu Thr Lys Val
                20                  25                  30
```

-continued

| | | | | | | | | | | | | | |
|---|---|---|---|---|---|---|---|---|---|---|---|---|---|
|Asn|Ala|Thr|Glu|Pro|Glu|Arg|Thr|Ala|Met|Lys|Lys|Ile|Gln|Asp|Cys|
| | |35| | | |40| | | |45| | | | |

Tyr Val Glu Asn Gly Leu Ile Ser Arg Val Leu Asp Gly Leu Val Met
    50              55                  60

Thr Thr Ile Ser Ser Ser Lys Asp Cys Met Gly Glu Ala Val Gln Asn
65              70              75                      80

Thr Val Glu Asp Leu Lys Leu Asn Thr Leu Gly Arg Glu Ile Cys Pro
            85              90                  95

Ala Val Lys Arg Asp Val Asp Leu Phe Leu Thr Gly Thr Pro Asp Glu
            100             105                 110

Tyr Val Glu Gln Val Ala Gln Tyr Lys Ala Leu Pro Val Val Leu Glu
    115             120                 125

Asn Ala Arg Ile Leu Lys Asn Cys Val Asp Ala Lys Met Thr Glu Glu
    130             135             140

Asp Lys Glu Asn Ala Leu Ser Leu Leu Asp Lys Ile Tyr Thr Ser Pro
145             150             155                 160

Leu Cys Leu Ile Asn Glu Pro Arg Gly Pro Thr Ile Lys Pro Cys Pro
            165             170             175

Pro Cys Lys Cys Pro Ala Pro Asn Leu Leu Gly Gly Pro Ser Val Phe
        180             185             190

Ile Phe Pro Pro Lys Ile Lys Asp Val Leu Met Ile Ser Leu Ser Pro
    195             200             205

Ile Val Thr Cys Val Val Val Asp Val Ser Glu Asp Pro Asp Val
    210             215             220

Gln Ile Ser Trp Phe Val Asn Asn Val Glu Val His Thr Ala Gln Thr
225             230             235                 240

Gln Thr His Arg Glu Asp Tyr Asn Ser Thr Leu Arg Val Val Ser Ala
            245             250             255

Leu Pro Ile Gln His Gln Asp Trp Met Ser Gly Lys Glu Phe Lys Cys
            260             265             270

Lys Val Asn Asn Lys Asp Leu Pro Ala Pro Ile Glu Arg Thr Ile Ser
    275             280             285

Lys Pro Lys Gly Ser Val Arg Ala Pro Gln Val Tyr Val Leu Pro Pro
    290             295             300

Pro Glu Glu Glu Met Thr Lys Lys Gln Val Thr Leu Thr Cys Met Val
305             310             315                 320

Thr Asp Phe Met Pro Glu Asp Ile Tyr Val Glu Trp Thr Asn Asn Gly
            325             330             335

Lys Thr Glu Leu Asn Tyr Lys Asn Thr Glu Pro Val Leu Asp Ser Asp
            340             345             350

Gly Ser Tyr Phe Met Tyr Ser Lys Leu Arg Val Glu Lys Lys Asn Trp
            355             360             365

Val Glu Arg Asn Ser Tyr Ser Cys Ser Val Val His Glu Gly Leu His
    370             375             380

Asn His His Thr Thr Lys Ser Phe Ser Arg Thr Pro Gly Lys
385             390             395

DIAGNOSTIC TESTS AND METHODS FOR ASSESSING SAFETY, EFFICACY OR OUTCOME OF ALLERGEN-SPECIFIC IMMUNOTHERAPY (SIT)

This application is a US National Stage application of PCT/US2014/052295, filed 22 Aug. 2014, which claims priority to U.S. Provisional patent application Ser. No. 61/869,214, filed 23 Aug. 2013, the contents of all of which are hereby incorporated by reference in their entireties.

FIELD OF THE INVENTION

The present invention relates to diagnostic tests and assay methods for determining the safety, efficacy, or outcome of allergen-specific immunotherapy.

BACKGROUND

Allergies and allergic diseases are serious medical conditions with consequences ranging from non-life threatening responses that resolve over time to life threatening effects such as anaphylaxis. Allergic reactions can result from contact or exposure to a variety of products such as certain food items, insect venom, plant-derived material (e.g., pollen), chemicals, drugs/medications, and animal dander.

Current treatment options for allergies include avoidance of the allergen where possible, the use of anti-allergy medications to treat the symptoms (e.g. antihistamines and corticosteroids) and prophylaxis using allergen-specific immunotherapy (SIT). These current treatment strategies are often inadequate, costly, impractical or involve significant risk. For example, avoidance of allergen is not always possible and can negatively impact on patient and caregiver quality of life. Medications used to treat allergies ameliorate the symptoms, but do not stop the progression. The only therapy that modifies progression of allergies is allergen-specific immunotherapy (SIT). However, SIT has several disadvantages in that it requires numerous allergen administrations over a 3 to 5 year period and can cause severe adverse events that range from local allergic reactions to anaphylaxis (Hedlin, et al. (1991), J. Allergy Clin. Immunol. 87:955-64; Hedlin, et al., (1986), J. Allergy Clin. Immunol. 77:488-96).

Given the potential risks associated with allergen-specific immunotherapy, it would be beneficial to be able to assess the safety, efficacy, or outcome of allergen-specific immunotherapy during the treatment period and/or at the time of completion of therapy. Such a test or assay method would provide information as to whether the patient is responding to treatment, and as such, it may also allow for a determination as to whether the patient will be adequately protected by SIT. Such a test or assay method would also aid in the determination of when a patient can initiate or terminate maintenance therapy. Currently there are no quantitative tests that aid in these safety or efficacy determinations. Accordingly, an unmet need exists in the art for development of such a diagnostic test, or an assay method for determining the safety, efficacy, or outcome of allergen-specific immunotherapy.

BRIEF SUMMARY OF THE INVENTION

In a first aspect the present invention provides a diagnostic test for determining the safety, efficacy, or outcome of allergen-specific immunotherapy (SIT) in a patient, the test comprising:

(a) obtaining a tissue sample, or an extract thereof, a biological fluid, or a blood sample from a patient undergoing allergen-specific immunotherapy (SIT);
(b) quantitating total IgG, allergen-specific IgG, and allergen-specific IgE from any one or more of the samples of (a);
(c) reacting the allergen-specific IgG from step (b) with the allergen for which the patient is undergoing SIT, plus allergen-specific IgE; and
(d) measuring either
    (i) the amount of allergen-specific IgG in the tissue sample, or an extract thereof, in the biological fluid, or in the blood sample obtained from the patient that is bound to the allergen, or
    (ii) the amount of allergen-specific IgE displaced or prevented from binding to allergen by the allergen-specific IgG contained in the tissue sample, or extract thereof, or the biological fluid, or the blood sample from the patient, wherein the amount of allergen-specific IgG in the tissue sample, or extract thereof, or the biological fluid, or the blood sample from the patient bound to the allergen is directly proportional to the safety, efficacy, or outcome of allergen-specific immunotherapy (SIT) in a patient, or wherein the amount of allergen-specific IgE bound to the allergen and subsequently displaced or prevented from binding to allergen by the allergen-specific IgG contained in the tissue sample, or extract thereof, or the biological fluid, or the blood sample from the patient is directly proportional to the safety, efficacy, or outcome of allergen-specific immunotherapy (SIT) in a patient.

In one embodiment, the diagnostic test may be performed in vitro or in vivo.

In one embodiment, the tissue sample obtained from the patient undergoing SIT may be any tissue sample, or extract thereof, biological fluid, or blood sample containing immunoglobulin expressing cells.

In a related embodiment, the tissue sample obtained from the patient undergoing SIT may be a whole blood sample, or serum, or plasma.

In one embodiment, the binding of allergen-specific IgG from the patient's tissue sample, or extract thereof, or biological fluid, or blood sample, to the allergen, or the amount of allergen-specific IgE displaced or prevented from binding to allergen by the allergen-specific IgG in the patient's tissue sample, or extract thereof, or biological fluid, or blood sample is determined by an in vitro method selected from the group consisting of an enzyme-linked immunosorbent assay (ELISA), a radioimmunoassay (RIA), an immunoradiometric assay (IRMA), a luminescence immunoassay (LIA), an immunoblot, FACs analysis, an IgE-facilitated allergen binding (FAB) assay, and an assay using an engineered cell line expressing FcεR1.

In one embodiment, the diagnostic test may be performed in vivo in an allergen-specific animal model, wherein the binding of allergen-specific IgG from the patient's tissue sample, or extract thereof, or biological fluid, or blood sample, to the allergen, or the amount of allergen-specific IgE displaced or prevented from binding to allergen by the allergen-specific IgG in the patient's tissue sample, or extract thereof, or biological fluid, or blood sample is determined.

In one embodiment, the in vivo diagnostic test is performed in an animal model of passive cutaneous anaphylaxis (PCA).

In a related aspect the invention provides a diagnostic test for determining the safety, efficacy, or outcome of allergen-specific immunotherapy (SIT) in a patient, the test comprising:

(a) a tissue sample, or extract thereof, a biological fluid, or a blood sample from a patient who is undergoing, or has completed allergen-specific immunotherapy;

(b) an allergen sample that corresponds to the allergen for which the patient is undergoing SIT;

(c) an allergen-specific IgE;

(d) a receptacle for mixing the reagents of step (a) through step (c);

(e) reagents for measuring either the amount of allergen-specific IgG in the patient's tissue sample, or extract thereof, or biological fluid, or blood sample bound to the allergen, or for measuring the amount of allergen-specific IgE displaced or prevented from binding to allergen by the allergen-specific IgG contained in the patient tissue sample, or extract thereof, or biological fluid, or blood sample after mixing a sample from (a) with the reagents of (b) and (c); and (f) directions for measuring the amount of allergen-specific IgG bound to the allergen, or for measuring the amount of allergen-specific IgE displaced or prevented from binding to allergen by the allergen-specific IgG contained in the patient tissue sample, or extract thereof, or biological fluid, or blood sample, wherein the amount of allergen-specific IgG contained in the patient tissue sample, or extract thereof, or biological fluid, or blood sample of (a) bound to the allergen is directly proportional to the safety, efficacy, or outcome of allergen-specific immunotherapy (SIT) in a patient, or wherein the amount of allergen-specific IgE bound to the allergen and subsequently displaced or prevented from binding to allergen by the allergen-specific IgG contained in the patient tissue sample, or extract thereof, or biological fluid, or blood sample of (a) is directly proportional to the safety, efficacy, or outcome of allergen-specific immunotherapy (SIT) in a patient.

In a related aspect the invention provides a test kit for determining if a patient is responsive to allergen-specific immunotherapy (SIT), the kit comprising:

(a) a first reagent containing the allergen for which allergen-specific immunotherapy is being administered;

(b) a second reagent containing allergen-specific IgE;

(c) third reagent containing an allergen-specific IgG as a known positive standard;

(d) reagents for measuring the amount of allergen-specific IgG or IgE;

(e) a receptacle for collecting a tissue sample, or extract thereof, a biological fluid, or a blood sample from a patient undergoing SIT, or who has completed SIT; and (f) instructions for use of the kit.

In one embodiment, the first reagent in the test kit is provided on a solid phase support.

In one embodiment, the second reagent in the test kit is provided on a solid phase support.

In one embodiment the first reagent in the test kit may contain a detectable label.

In one embodiment the second reagent in the test kit may contain a detectable label.

In one embodiment, the second reagent in the test kit is an allergen-specific IgE containing a detectable label.

In one embodiment, IgE from a cat allergic patient is captured on a solid support and labeled allergen is mixed together with SIT IgG and the amount of allergen not bound by SIT IgG is detected after binding to the IgE on the solid support.

In one embodiment, the detectable label is selected from the group consisting of a fluorescence label, a radiolabel, an enzyme label, a luminescent label, an electrochemical, or a visual label.

In one embodiment, the diagnostic tests and test kits may be useful for measuring a response in a patient undergoing SIT for an allergen selected from the group consisting of an animal product, a food allergen, plant pollen, mold spores, house dust mites, cockroaches, perfume, detergents, household cleaners, latex, a drug product, or insect venom.

In one embodiment, the animal product is selected from the group consisting of animal fur, animal dander, wool, and mite excretions.

In one embodiment, the animal product contains the allergen Fel d1.

In one embodiment, the animal product contains the allergen can f1, can f2, can f3, can f4, can f5 or can f6.

In one embodiment, the food allergen is selected from the group consisting of eggs, meat, fruit, legumes, milk or other dairy products, seafood, sesame, soy, wheat, oat, barley, celery and celeriac, corn or maize and tree nuts.

In one embodiment, the legumes are selected from the group consisting of peanuts, beans, peas and soybeans.

In one embodiment, the tree nuts are selected from the group consisting of pecans, almonds, cashews, hazelnuts (filberts), walnuts, brazil nuts, macadamia nuts, chestnuts, pine nuts and pistachio nuts.

In one embodiment, the plant pollen is selected from the group consisting of grass pollen, weed pollen and tree pollen.

In one embodiment, the tree pollen is selected from the group consisting of birch pollen, cedar pollen, oak pollen, alder pollen, hornbeam pollen, aesculus pollen, willow pollen, poplar pollen, plantanus pollen, tilia pollen, olea pollen, Ashe juniper pollen, and *Alstonia scholaris* pollen.

In one embodiment, the birch pollen contains the allergen Betv 1.

In one embodiment, the cedar pollen contains the allergen Cryj1 or Cryj2.

In one embodiment, the grass pollen is ryegrass or timothy-grass.

In one embodiment, the weed pollen is selected from the group consisting of ragweed, plantago, nettle, *Artemisia vulgaris, Chenopodium album* and sorrel.

In one embodiment, the insect venom is produced by bees, wasps or fire ants.

In one embodiment, the allergen-specific IgE used in the diagnostic test may be selected from the group consisting of an allergen-specific IgE obtained from the patient undergoing SIT, an allergen-specific IgE obtained from another allergen-injected mammal, and a recombinant IgE specific for the allergen.

In one embodiment, the steps of any of the diagnostic tests described above may further include injecting a sample of the patient's tissue sample or extract thereof, or biological fluid, or blood sample into an allergen-specific animal model to assess the protective efficacy of the allergen-specific IgG from the patient, wherein protection of the animal following challenge with the allergen is indicative of the safety, efficacy or outcome of SIT in the patient.

In one embodiment, the animal model is a mouse model of Passive Cutaneous Anaphylaxis (PCA) and wherein the model comprises the following steps:

(a) injecting the animal with allergen-specific IgE, or antiserum containing allergen-specific IgE, intradermally at one skin site and injecting the animal with non-allergen-specific IgE or antiserum containing non-allergen-specific IgE intradermally at a second different skin site;
(b) injecting the animal systemically with the allergen for which the patient is undergoing, or has undergone SIT therapy, along with a dye; and
(c) assessing the extent of dye extravasation at the site of allergen injection;

wherein the amount of dye extravasated into the tissue is directly related to the amount of mast cell activation in the animal and wherein a decrease in the amount of dye extravasated into the tissue is indicative of safety, efficacy, or a positive outcome of allergen-specific immunotherapy in the patient.

A second aspect of the invention provides a method for assessing the safety, efficacy, or outcome of allergen-specific immunotherapy, the method comprising assessing the level of allergen-specific IgG in a patient tissue sample, or extract thereof, or biological fluid, or blood sample using any of the diagnostic tests or test kits noted herein, followed by confirmation of the in vitro results by measuring the protective efficacy of the allergen-specific IgG from the patient in an allergen-specific animal model, wherein elevated levels of allergen-specific IgG from the patient's serum and protection of the animal following challenge with the allergen is indicative of safety, efficacy, or a positive outcome of SIT.

In a related aspect, the invention provides a direct in vivo method for assessing the safety, efficacy, or outcome of allergen-specific immunotherapy (SIT) in a patient, the method comprising injecting a sample containing allergen-specific IgG from the patient into an allergen-specific animal model to determine the protective efficacy of the allergen-specific IgG from the patient, without the need to assess the patient's tissue sample, or biological fluid sample or blood sample in an in vitro assay prior to the in vivo animal model, wherein protection of the animal following challenge with the allergen is indicative of safety, efficacy, or a positive outcome of allergen-specific immunotherapy in the patient.

Any allergy animal model known to those skilled in the art to assess the safety, efficacy or outcome of SIT may be used, although in one embodiment, the animal model that is used herein to assess safety, efficacy, or the outcome of SIT is a mouse model of Passive Cutaneous Anaphylaxis (PCA) and wherein the model comprises the following steps:
(a) injecting the animal with allergen-specific IgE, or antiserum containing allergen-specific IgE, intradermally at one skin site and injecting the animal with non-allergen-specific IgE or antiserum containing non-allergen-specific IgE intradermally at a second different skin site;
(b) injecting the animal systemically with the allergen for which the patient is undergoing, or has undergone SIT therapy, along with a dye; and
(c) assessing the extent of dye extravasation at the site of allergen injection;

wherein the amount of dye extravasated into the tissue is directly related to the amount of mast cell activation in the animal and wherein a decrease in the amount of dye extravasated into the tissue is indicative of safety, efficacy, or a positive outcome of allergen-specific immunotherapy in the patient.

In one embodiment, the methods for assessing safety, efficacy, or outcome of SIT may be used to assess patients receiving such therapy for an allergen selected from the group consisting of an animal product, a food allergen, plant pollen, mold spores, house dust mites, cockroaches, perfume, detergents, household cleaners, latex, a drug product, or insect venom.

In one embodiment, the animal product is selected from the group consisting of animal fur, animal dander, wool, and mite excretions.

In one embodiment, the animal product contains the allergen Fel d1.

In one embodiment, the animal product contains the allergen can f1, can f2, can f3, can f4, can f5 or can f6.

In one embodiment, the food allergen is selected from the group consisting of eggs, meat, fruit, legumes, milk or other dairy products, seafood, sesame, soy, wheat, oat, barley, celery and celeriac, corn or maize and tree nuts.

In one embodiment, the legumes are selected from the group consisting of peanuts, beans, peas and soybeans.

In one embodiment, the tree nuts are selected from the group consisting of pecans, almonds, cashews, hazelnuts (filberts), walnuts, brazil nuts, macadamia nuts, chestnuts, pine nuts and pistachio nuts.

In one embodiment, the plant pollen is selected from the group consisting of grass pollen, weed pollen and tree pollen.

In one embodiment, the tree pollen is selected from the group consisting of birch pollen, cedar pollen, oak pollen, alder pollen, hornbeam pollen, aesculus pollen, willow pollen, poplar pollen, plantanus pollen, tilia pollen, olea pollen, Ashe juniper pollen, and *Alstonia scholaris* pollen.

In one embodiment, the birch pollen contains the allergen Betv 1.

In one embodiment, the cedar pollen contains the allergen Cryj1 or Cryj2.

In one embodiment, the grass pollen is ryegrass or timothy-grass.

In one embodiment, the weed pollen is selected from the group consisting of ragweed, plantago, nettle, *Artemisia vulgaris, Chenopodium album* and sorrel.

In one embodiment, the insect venom is produced by bees, wasps or fire ants.

In a related aspect, the invention provides for determining if allergen-specific immunotherapy induces allergen-specific immunoglobulins that are protective in a mammal upon challenge of the mammal with the allergen, the method comprising measuring the level of allergen-specific IgG in a patient tissue sample, or extract thereof, or biological fluid, or blood sample using any of the diagnostic tests or test kits described herein, and assessing the protective efficacy of the allergen-specific IgG from the patient tissue sample, or extract thereof, or biological fluid, or blood sample in an allergen-specific animal model, such as the PCA model described herein and in Example 1, wherein a decrease in mast cell degranulation as evidenced in this model indicates that the allergen-specific immunoglobulins generated during SIT are protective against subsequent challenge with the allergen and that the allergen-specific immunotherapy was effective.

A third aspect of the invention provides a method of screening a patient to determine if the patient has responded to allergen specific immunotherapy (SIT), or will be adequately protected by SIT, or for determining when a patient can initiate or terminate maintenance therapy, the method comprising measuring the level of allergen-specific IgG in a patient tissue sample, or extract thereof, or biological fluid, or blood sample using any of the diagnostic tests or test kits described herein, and assessing the protective efficacy of the allergen-specific IgG from the patient tissue sample, or extract thereof, or biological fluid, or blood sample in an allergen-specific animal model, wherein elevated levels of allergen-specific IgG from the patient's tissue sample, or extract thereof, or biological fluid, or blood sample and protection of the animal following challenge with the allergen is indicative that the patient has responded to allergen specific immunotherapy (SIT), or will be adequately protected by SIT, or that the patient can initiate or terminate maintenance therapy.

A fourth aspect of the invention provides a method of determining if a patient suffering from an allergy is responsive to therapy with one or more antibodies or antigen binding fragments thereof specific for the allergen, the method comprising:
- a) collecting a sample of tissue or an extract thereof, or a biological fluid, or a blood sample from a patient suffering from an allergy;
- b) extracting allergen specific IgE from any one or more of the patient samples of (a);
- c) mixing the IgE from the patient sample with the allergen and with one or more antibodies or antigen binding fragments thereof specific for the allergen; and
- d) determining if the addition of the antibodies or antigen binding fragments thereof specific for the allergen blocks the binding of the allergen specific IgE from step b) to the allergen, wherein the ability of the one or more antibodies or antigen binding fragments thereof specific for the allergen to block the binding of allergen specific IgE from step b) to the allergen is indicative that the patient suffering from an allergy is responsive to therapy with the one or more antibodies specific for the allergy.

In one embodiment, the allergen is a cat allergen.

In one embodiment, the cat allergen is Fel d1.

In one embodiment, the one or more antibodies specific for the allergen are human monoclonal antibodies that bind specifically to Fel d1, wherein the one or more antibodies comprise the heavy chain complementary determining regions (HCDRs) of a heavy chain variable region (HCVR) comprising the amino acid sequence of SEQ ID NO: 2 or 18 and the light chain complementarity determining regions (LCDRs) of a light chain variable region (LCVR) comprising the amino acid sequence of SEQ ID NO: 10 or 26.

In one embodiment, the one or more human monoclonal antibodies or antigen binding fragments that bind specifically to Fel d1 comprise three HCDRs (HCDR1, HCDR2 and HCDR3) and three LCDRs (LCDR1, LCDR2 and LDR3), wherein the HCDR1 comprises the amino acid sequence of SEQ ID NO: 4 or 20; the HCDR2 comprises the amino acid sequence of SEQ ID NO: 6 or 22; the HCDR3 comprises the amino acid sequence of SEQ ID NO: 8 or 24; the LCDR1 comprises the amino acid sequence of SEQ ID NO: 12 or 28; the LCDR2 comprises the amino acid sequence of SEQ ID NO: 14 or 30; and the LCDR3 comprises the amino acid sequence of SEQ ID NO: 16 or 32.

In one embodiment, the one or more human monoclonal antibodies that bind specifically to Fel d1 comprises a HCVR comprising the amino acid sequence of SEQ ID NO: 2 or 18 and a LCVR comprising the amino acid sequence of SEQ ID NO: 10 or 26.

In one embodiment, the one or more human monoclonal antibodies that bind specifically to Fel d1 comprise the HCVR/LCVR amino acid sequence pairs of SEQ ID NOs: 2/10 or SEQ ID NOs:18/26.

In one embodiment, a composition comprising two anti-Fel d1 monoclonal antibodies may be used for treating cat allergic patients, wherein the two Fel d1 human monoclonal antibodies have HCVR/LCVR amino acid sequence pairs of SEQ ID NOs: 2/10 and SEQ ID NOs:18/26. The diagnostic tests and methods described herein may be used to determine if a patient suffering from a cat allergy is responsive to therapy with these antibodies, or with other antibodies that have the same or a similar binding specificity.

In one embodiment, the results obtained from the in vitro study noted above, may be further confirmed in an animal allergy model, such as the Passive Cutaneous Anaphylaxis (PCA) model.

This model comprises the following steps:
- (a) injecting the animal with allergen-specific IgE, or antiserum containing allergen-specific IgE, intradermally at one skin site and injecting the animal with non-allergen-specific IgE or antiserum containing non-allergen-specific IgE intradermally at a second different skin site;
- (b) injecting the animal systemically with the allergen for which the patient is undergoing, or has undergone SIT therapy, along with a dye; and
- (c) assessing the extent of dye extravasation at the site of allergen injection;

wherein the amount of dye extravasated into the tissue is directly related to the amount of mast cell activation in the animal and wherein a decrease in the amount of dye extravasated into the tissue is indicative of safety, efficacy, or a positive outcome of allergen-specific immunotherapy in the patient.

DETAILED DESCRIPTION

Figure 1:
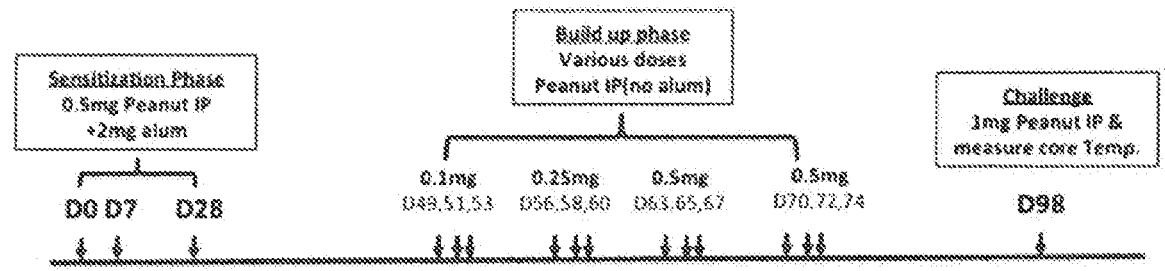
FIG. 1. Panel (A) depicts a schematic of a peanut specific immunotherapy mouse model that was used to generate peanut specific antisera containing peanut specific IgG. Panel B shows the extent of anaphylaxis in two groups of experimental mice as a means to determine the efficacy of the antigen specific immunotherapy. This is assessed in terms of a core temperature decrease. Mice receiving no SIT are designated black dashes with squares; mice not undergoing SIT are designated with grey triangles.
Figure 1:
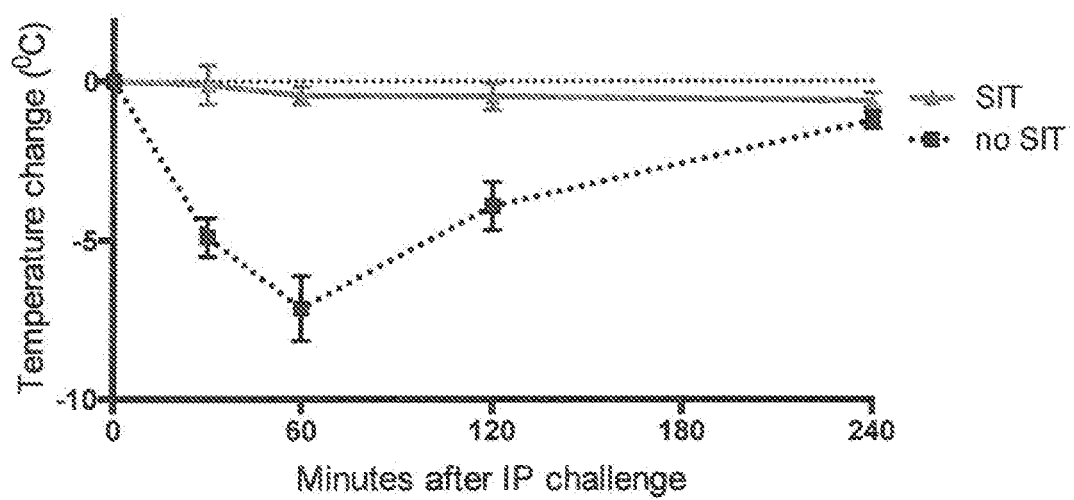

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All patents, applications and non-patent publications mentioned in this specification are incorporated herein by reference in their entireties. Other embodiments will become apparent from a review of the ensuing detailed description.

Definitions

As used herein, the expressions "allergen-specific immunotherapy," "specific immunotherapy," "SIT," "SIT regimen," and the like, refer to the repeated administration of an allergen to a subject over time as means for treating or preventing allergies and allergic reactions, or to reduce or eliminate allergic responses. Subcutaneous immunotherapy uses a protocol of weekly injections with gradually increasing dosages of allergen extract until a maintenance dose is achieved. Subsequently the maintenance dose administration is reduced to biweekly and then to monthly intervals for a period of 3 to 5 years (See J. Allergy Clin. Immunol. (2007), 120:S25-85). More recent studies have been conducted to administer the allergen sublingually.

To measure the "safety", "efficacy" or "outcome" of SIT, various clinical measurements have historically been utilized. The "safety" of SIT generally takes into account any untoward allergic reaction to the allergen being administered. The allergic reaction may be mild or may be severe following allergen administration. The "efficacy" or "outcome" of SIT takes into account several clinical parameters, including a measurement of symptoms (with emphasis on alleviating the symptoms associated with the particular allergen exposure) and the need for concomitant medications. Both physician rated and patient self rated scores have been implemented in clinical trials. The use of questionnaires for evaluating the quality of life are generally used as secondary outcome parameters. Skin prick tests are also utilized as a means of assessing efficacy/outcome of therapy.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, wheat, soy, fish, shellfish, peanuts and tree nuts. Alternatively, an allergen may be contained within or derived from a non-food item such as, e.g., dust (e.g., containing dust mite), pollen, insect venom (e.g., venom of bees, wasps, mosquitos, etc.), mold, animal dander, latex, medication, drugs, ragweed, grass and birch.

As used herein, the phrases "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production and/or increased allergen-specific immunoglobulin production.

The term "up-dosing" means a period of treatment during which the doses of allergen administered are gradually increased to reach a full dose level, which is used in the following maintenance phase, and the up-dosing phase ends when the full dose level is reached, i.e. immediately subsequent to the administration of the first full dose.

"Maintenance phase" or "maintenance therapy" means a period of treatment in continuation of the up-dosing phase and during which a full dose of allergen is administered, the maintenance phase starting immediately subsequent to the administration of the first full dose.

"Mast cell", as used herein refers to one or more mast cells, basophils, and other cells with IgE receptors.

"Sensitized animal" refers to an animal having adapted an immunological state so that, when it encounters an antigen, it has a response similar to that observed in allergic humans. This may include a reaction to an allergen resulting in any one or more of the following symptoms and/or reactions: cutaneous reactions, wheezing and labored respiration, a higher percentage of degranulated mast cells, increased histamine levels upon challenge with allergen, an increase in the level of antigen specific IgG in the animal after sensitization, an increase in allergen specific IgE levels, or an anaphylactic reaction. "Desensitize" is defined herein as to decrease the allergic-reactivity of an allergen-sensitive individual to exposure to the allergen, (e.g., to a level less than that which the allergen-sensitive individual would otherwise experience).

The "Passive Cutaneous Anaphylaxis" or "PCA" animal model is a model used to assess in vivo mast cell degranulation (See Bradley, et al. (1991), J. Allergy Clin. Immunol. 88:661-74). The model relies on the passive transfer of antisera containing allergen-specific polyclonal IgE, which binds to FcεR1 on mast cells near the site of administration. The animals are effectively "sensitized" locally to the specific antigen. When antigen is subsequently injected systemically as an allergen challenge along with Evan's blue dye, antigen-induced mast cell degranulation results in rapid capillary dilation and increased vascular permeability that can be visualized and quantitated by measuring dye leakage into the reaction site.

As used herein, the terms "treat", "treating", or the like, mean to alleviate symptoms, eliminate the causation of symptoms either on a temporary or permanent basis, or to prevent or slow the appearance of symptoms of an allergic reaction.

As used herein, the term "a subject in need thereof" means any human or non-human animal who: (a) is prone to allergic reactions or responses when exposed to one or more allergens; (b) has previously exhibited an allergic response or reaction to one or more allergens; (c) has a known history of allergies; and/or (d) exhibits a sign or symptom of an allergic response or anaphylaxis.

The term "patient sample" may include any tissue sample, including both solid tissue (or extracts thereof), biological fluids, or blood samples. The blood sample may be whole blood, plasma or serum. The tissue sample or extract thereof, or biological fluid may be any tissue sample or bodily fluid that contains immunoglobulin expressing cells.

The term "Fel d1", "Fel d 1", or "FELD1", as used herein, refers to at least one Fel d1 protein, either in natural/native form, or recombinantly produced. The Fel d1 protein comprises, or alternatively consists of, chain 1 (also referred to as chain A) of Fel d1 (SEQ ID NO: 33) and chain 2 (also referred to as chain B) of Fel d1 (SEQ ID NO: 34). The natural Fel d1 protein is an approximately 18 kDa heterodimeric glycoprotein composed of two chains derived from two independent genes (See Duffort, O. A. et al., (1991), Mol. Immunol. 28:301-309; Kristensen, A. K. et al., (1997), Biol. Chem. 378:899-908; Kaiser L. et al. (2003), J. Biol. Chem. 278(39):37730-37735). The amino acid sequence of chain 1 of Fel d1 is also provided in GenBank as accession number P30438, or as accession number NP_001041618.1, which also include the signal peptide which is removed in the mature protein. The amino acid sequence of chain 2 of Fel d1 is also provided in GenBank as accession number P30440, or as accession number NP_001041619.1, which include the signal peptide which is removed in the mature protein. A recombinant form of Fel d1 produced with a C-terminal myc-myc-hexahistidine tag (Fel d1mmH) is shown as SEQ ID NO: 52, wherein the Fel d1 B chain and Fel d1 A chain are linked as a continuous, in-line fusion with Fel d1 at the N terminus and the myc-myc-his tag at the C terminus. Another recombinant form of Fel d1 is produced with a C-terminal mouse Fc tag (Fel d1mFc) and is shown as SEQ ID NO: 53. (See Fel d1 B chain at accession number NP_001041619.1, amino acids 18-109 and Fel d1 A chain at accession number NP_001041618.1, amino acids 19-88 with a D27G mutation).

A human FcεR1α was produced with a terminal mouse Fc tag and this is shown as SEQ ID NO: 51. (See also accession number NP_001992 (V26-E205) with the C terminal mouse IgG2a Fc tag (98-330 of P01863).

The term "antibody", as used herein, means any antigen-binding molecule or molecular complex comprising at least one complementarity determining region (CDR) that specifically binds to or interacts with a particular antigen (e.g., Fel d1). The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. (2002), J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human (recombinant, not naturally occurring) monoclonal antibodies that specifically bind to Fel d1, as disclosed herein, may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human monoclonal antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, may include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The antibodies used in the methods of the present invention may be recombinant, non-naturally occurring human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Allergen-Specific Immunotherapy (SIT)

As used herein, the expressions "allergen-specific immunotherapy," "specific immunotherapy," "SIT," "SIT regimen," and the like, refer to the repeated administration of an allergen to a subject over time as means for treating or preventing allergies and allergic reactions, or to reduce or eliminate allergic responses. In a typical SIT regimen, small amounts of allergen are initially administered to an allergic subject, followed by administration of increased amounts of allergen. In certain instances, the SIT regimen comprises at least two consecutive phases: (1) an up-dosing phase, and (2) a maintenance phase. In the up-dosing phase, increasing doses of allergen are administered until an effective and safe dose is achieved. The dose that is established at the end of the up-dosing phase is then administered to the subject throughout the course of the maintenance phase. The duration of the up-dosing phase can be several weeks or several months. In certain embodiments, however, the up-dosing phase is of substantially shorter duration (e.g., less than one week, less than 6 days, less than 5 days, less than 4 days, less than 3 days, or less than 2 days). SIT regimens comprising an up-dosing phase of less than 5 days are sometimes referred to as "Rush" immunotherapy or "Rush SIT." The maintenance phase of an SIT regimen can last several weeks, several months, several years, or indefinitely.

Methods for Determining the Safety, Efficacy, or Outcome Following Allergen-Specific Immunotherapy (SIT)

Historically, variability in safety and clinical efficacy has limited the widespread application of SIT. However, more recent studies have attempted to better characterize the active ingredients by measurement of protein content, determination of biological activity, estimation of the predominant allergen that makes up the composition and the production of pure allergen molecules with the aid of recombinant DNA technology. Safety concerns using the subcutaneous route of allergen injection resulted in more recent studies to assess the sublingual route of allergen delivery and to characterize the immunological response to the allergen delivered via this route. While it appears that sublingual SIT is clearly efficacious and is associated with a favorable safety profile, efficacy appears to be lower than that of subcutaneous SIT. The better safety profile may be attributed to the presence of fewer mast cells in the oral mucosa, or to the delivery of smaller immunologically active doses of allergen, despite the larger dose that is administered. However, if larger doses are delivered via the sublingual route, this may alter the safety profile such that it is similar to SIT using the subcutaneous route of allergen injection. So the improvement in clinical efficacy may also result in a reduction in the safety profile. Because of the safety concerns, as well as non-compliance associate with SIT, it would be beneficial to be able to assess if the patient is responding to therapy early in the course of SIT, and if so, whether the patient may initiate or terminate maintenance therapy sooner rather than later.

As a general rule, in order to measure the "safety", "efficacy" or "outcome" of SIT, various clinical assessments have historically been utilized. The "safety" of SIT generally takes into account any untoward allergic reaction to the allergen being administered. The allergic reaction may be mild after allergen administration, or it may be severe following allergen administration. To measure the "efficacy" or "outcome" of SIT, several clinical parameters are generally taken into account, including a measurement of symptoms (with an emphasis on alleviating the symptoms associated with the particular allergen exposure after immunotherapy is completed) and the need for concomitant medications. In addition, both physician rated and patient self rated scores have been implemented in clinical trials. The use of questionnaires for evaluating the quality of life are generally used as secondary outcome parameters. Skin prick tests are also utilized as a means of assessing efficacy/outcome of therapy. None of the methods employed take into account a quantitative means of assessing whether the patient is actually responding to the particular therapy, or if they have responded, whether the protection attributed to SIT is sufficient or adequate to confer protection against future allergen exposure.

One aspect of the present invention provides methods for determining the safety, efficacy, or outcome of allergen-specific immunotherapy. The methods comprise obtaining a tissue sample, or extract thereof, or a biological fluid, or a blood sample from a patient who is undergoing SIT and using various in vitro and in vivo assays for assessing whether the patient is responding, or has responded to such therapy.

One embodiment of the invention provides a diagnostic test for determining the safety, efficacy, or outcome of allergen-specific immunotherapy (SIT) in a patient, the test comprising:

(a) obtaining a tissue sample, or an extract thereof, a biological fluid, or a blood sample from a patient undergoing allergen-specific immunotherapy (SIT);
(b) quantitating total IgG, allergen-specific IgG, and allergen-specific IgE from any one or more of the samples of (a);
(c) reacting the allergen-specific IgG from step (b) with the allergen for which the patient is undergoing SIT, plus allergen-specific IgE; and
(d) measuring either
  (i) the amount of allergen-specific IgG in the tissue sample, or an extract thereof, in the biological fluid, or in the blood sample obtained from the patient that is bound to the allergen, or
  (ii) the amount of allergen-specific IgE displaced or prevented from binding to allergen by the allergen-specific IgG contained in the tissue sample, or extract thereof, or the biological fluid, or the blood sample from the patient,
wherein the amount of allergen-specific IgG in the tissue sample, or extract thereof, or the biological fluid, or the blood sample from the patient bound to the allergen is directly proportional to the safety, efficacy, or outcome of allergen-specific immunotherapy (SIT) in a patient, or
wherein the amount of allergen-specific IgE bound to the allergen and subsequently displaced or prevented from binding to allergen by the allergen-specific IgG contained in the tissue sample, or extract thereof, or the biological fluid, or the blood sample from the patient is directly proportional to the safety, efficacy, or outcome of allergen-specific immunotherapy (SIT) in a patient.

The tissue sample obtained for the diagnostic test may be a solid tissue sample, or an extract thereof, or it may be a biological/bodily fluid. The sample may also be a blood sample. Whole blood may be used, or serum or plasma may be used in the assay. In one embodiment, the tissue sample contains immunoglobulin containing cells.

The binding of allergen-specific IgG from the patient's tissue sample, or extract thereof, or biological fluid, or blood sample, to the allergen, or the amount of allergen-specific IgE displaced or prevented from binding to allergen by the allergen-specific IgG in the patient's tissue sample, or extract thereof, or biological fluid, or blood sample may be determined by an in vitro method selected from the group consisting of an enzyme-linked immunosorbent assay (ELISA), a radioimmunoassay (RIA), an immunoradiometric assay (IRMA), a luminescence immunoassay (LIA), an immunoblot., FACs analysis, an IgE-facilitated allergen binding (FAB) assay (See Shamji, et al. (2006), J. Immunol. Methods, 317(1-2):71-79), and an assay using an engineered cell line expressing FcεR1.

Alternatively, the binding of allergen-specific IgG from the patient's tissue sample, or extract thereof, or biological fluid, or blood sample, to the allergen, or the amount of allergen-specific IgE displaced or prevented from binding to allergen by the allergen-specific IgG in the patient's tissue sample, or extract thereof, or biological fluid, or blood sample is determined in vivo using an allergen-specific animal model.

In one embodiment, the allergen-specific animal model is a mouse model of Passive Cutaneous Anaphylaxis (PCA), wherein the model comprises the following steps:
(a) injecting the animal with allergen-specific IgE, or antiserum containing allergen-specific IgE, intradermally at one skin site and injecting the animal with non-allergen-specific IgE or antiserum containing non-allergen-specific IgE intradermally at a second different skin site;
(b) injecting the animal systemically with the allergen for which the patient is undergoing, or has undergone SIT therapy, along with a dye; and
(c) assessing the extent of dye extravasation at the site of allergen injection;
wherein the amount of dye extravasated into the tissue is directly related to the amount of mast cell activation in the animal and wherein a decrease in the amount of dye extravasated into the tissue is indicative of safety, efficacy, or a positive outcome of allergen-specific immunotherapy in the patient.

In certain embodiments, the patient sample may be analyzed first in vitro using the methods and diagnostic tests described above, followed by a confirmatory analysis in the in vivo animal model, such as the PCA model described herein.

Alternatively, each assay (in vitro and in vivo) may be used as a stand-alone analytical tool for quantitating the patient response to SIT.

In one embodiment, the invention provides a diagnostic test for determining the safety, efficacy, or outcome of allergen-specific immunotherapy (SIT) in a patient, the test comprising:
(a) a tissue sample, or extract thereof, a biological fluid, or a blood sample from a patient who is undergoing, or has completed allergen-specific immunotherapy;
(b) an allergen sample that corresponds to the allergen for which the patient is undergoing SIT;
(c) an allergen-specific IgE;
(d) a receptacle for mixing the reagents of step (a) through step (c);
(e) reagents for measuring either the amount of allergen-specific IgG in the patient's tissue sample, or extract thereof, or biological fluid, or blood sample bound to the allergen, or for measuring the amount of allergen-specific IgE displaced or prevented from binding to allergen by the allergen-specific IgG contained in the patient tissue sample, or extract thereof, or biological fluid, or blood sample after mixing a sample from (a) with the reagents of (b) and (c); and
(f) directions for measuring the amount of allergen-specific IgG bound to the allergen, or for measuring the amount of allergen-specific IgE displaced or prevented from binding to allergen by the allergen-specific IgG contained in the patient tissue sample, or extract thereof, or biological fluid, or blood sample,
wherein the amount of allergen-specific IgG contained in the patient tissue sample, or extract thereof, or biological fluid, or blood sample of (a) bound to the allergen is directly proportional to the safety, efficacy, or outcome of allergen-specific immunotherapy (SIT) in a patient, or
wherein the amount of allergen-specific IgE bound to the allergen and subsequently displaced or prevented from binding to allergen by the allergen-specific IgG contained in the patient tissue sample, or extract thereof, or biological fluid, or blood sample of (a) is directly proportional to the safety, efficacy, or outcome of allergen-specific immunotherapy (SIT) in a patient.

In a related embodiment, the invention provides a test kit for determining if a patient is responsive to allergen-specific immunotherapy (SIT), the kit comprising:
(a) a first reagent containing the allergen for which allergen-specific immunotherapy is being administered;

(b) a second reagent containing allergen-specific IgE;
(c) a third reagent containing an allergen-specific IgG as a known positive standard;
(d) reagents for measuring the amount of allergen-specific IgG or IgE;
(e) a receptacle for collecting a tissue sample, or extract thereof, a biological fluid, or a blood sample from a patient undergoing SIT, or who has completed SIT; and
(f) instructions for use of the kit.

In one embodiment, the first reagent is provided on a solid phase support.

In one embodiment, the second reagent is provided on a solid support.

In one embodiment, the first reagent contains a detectable label.

In one embodiment, the second reagent contains a detectable label.

In one embodiment, the second reagent is an allergen-specific IgE containing a detectable label.

The detectable label may be selected from the group consisting of a fluorescence label, a radiolabel, an enzyme label, a luminescent label, an electrochemical, or a visual label.

The diagnostic tests described herein may be used to measure a response in a patient undergoing SIT for an allergen selected from the group consisting of an animal product, a food allergen, plant pollen, mold spores, house dust mites, cockroaches, perfume, detergents, household cleaners, latex, a drug product, or insect venom.

In one embodiment, the animal product is selected from the group consisting of animal fur, animal dander, wool, and mite excretions.

In one embodiment, the animal product contains the allergen Fel d1.

In one embodiment, the animal product contains the allergen can f1, can f2, can f3, can f4, can f5 or can f6.

In one embodiment, the food allergen is selected from the group consisting of eggs, meat, fruit, legumes, milk or other dairy products, seafood, sesame, soy, wheat, oat, barley, celery and celeriac, corn or maize and tree nuts.

In one embodiment, the legumes are selected from the group consisting of peanuts, beans, peas and soybeans.

In one embodiment, the tree nuts are selected from the group consisting of pecans, almonds, cashews, hazelnuts (filberts), walnuts, brazil nuts, macadamia nuts, chestnuts, pine nuts and pistachio nuts.

In one embodiment, the plant pollen is selected from the group consisting of grass pollen, weed pollen and tree pollen.

In one embodiment, the tree pollen is selected from the group consisting of birch pollen, cedar pollen, oak pollen, alder pollen, hornbeam pollen, aesculus pollen, willow pollen, poplar pollen, plantanus pollen, tilia pollen, olea pollen, Ashe juniper pollen, and *Alstonia scholaris* pollen.

In one embodiment, the birch pollen contains the allergen Betv 1.

In one embodiment, the cedar pollen contains the allergen Cryj1 or Cryj2

In one embodiment, the grass pollen is ryegrass or timothy-grass.

In one embodiment, the weed pollen is selected from the group consisting of ragweed, plantago, nettle, *Artemisia vulgaris, Chenopodium album* and sorrel.

In one embodiment, the insect venom is produced by bees, wasps or fire ants.

Accordingly, the methods for assessing the safety, efficacy or outcome of SIT may be done solely by an in vitro assay, as described herein using any of the diagnostic tests or kits described.

Alternatively, the methods for assessing the safety, efficacy or outcome of SIT may be done solely by an in vivo assay, such as the allergy model described herein (the PCA model), or any other animal allergy model known to those skilled in the art, which measures, for example, a decrease in any one or more allergy symptoms or allergic reactions, such as mast cell degranulation.

In one embodiment the in vitro assay and the in vivo allergy model (e.g., PCA model) may be run concurrently.

In one embodiment, the assessment of safety, efficacy, or outcome of SIT may be done as a two step process, the first measurement done by using one of the in vitro diagnostic tests described herein, and then confirmed using an in vivo allergy mode, e.g. the PCA model described in Example 1, whereby the patient's immunoglobulins after SIT are purified and injected directly into the animal model to see if they confer protection to the animal when the animal is challenged with the allergen.

In a related embodiment, the invention provides a method of screening a patient to determine if the patient has responded to allergen specific immunotherapy (SIT), or will be adequately protected by SIT, or for determining when a patient can initiate or terminate maintenance therapy, the method comprising measuring the level of allergen-specific IgG in a patient tissue sample, or extract thereof, or biological fluid, or blood sample using any of the diagnostic tests or test kits described above, and assessing the protective efficacy of the allergen-specific IgG from the patient tissue sample, or extract thereof, or biological fluid, or blood sample in an allergen-specific animal model, wherein elevated levels of allergen-specific IgG from the patient's tissue sample, or extract thereof, or biological fluid, or blood sample and protection of the animal following challenge with the allergen is indicative that the patient has responded to allergen specific immunotherapy (SIT), or will be adequately protected by SIT, or that the patient can initiate or terminate maintenance therapy.

Comparison of SIT with the Use of Therapeutic Antibodies Specific for the Allergen While allergen-specific immunotherapy is the only method available which actually alters the disease state in allergy prone individuals, there are times when such therapy may not be adequate or appropriate, such as in patients who cannot build up an adequate immune response to the allergen due to health issues, such as patients who are immunocompromised due to disease, illness, or immunosuppressive drug therapies. In those situations, it may be beneficial to utilize a therapeutic antibody approach to treat the allergy.

The approach of passively targeting allergens with allergen-specific monoclonal antibodies to block mast cell degranulation may prove to be an efficacious alternative to SIT. The study described herein utilized two such fully human monoclonal antibodies that bind specifically to the cat allergen, Fel d1. These two human monoclonal antibodies specific for Fel d1 were tested in the PCA model along with Fel d1 specific IgG purified from patients who had undergone SIT for cat allergy (See Example 1).

While the Fel d1 IgG from SIT patients was efficacious in this model, the ranges of inhibition of mast cell degranulation varied depending on the length of time SIT was administered. On the other hand, Fel d1 specific human monoclonal antibodies significantly inhibited mast cell degranulation in this model. More specifically, the Fel d1 monoclonal antibody cocktail was about 5-fold more potent than the SIT patient derived Fel d1 specific IgG based on total antibody mass dosage.

The fact that both the human monoclonal anti-Fel d1 antibodies and the Fel d1 specific immunoglobulin isolated from SIT patients demonstrated protection in the PCA model indicates that allergen-specific immunoglobulins play a role in altering a patient's response to allergen challenge. However, as noted previously, while both methods confer protection, the immunoglobulin derived from the SIT patients took years to develop in the patient in need of such therapy, while the human monoclonal antibodies can be administered immediately and thus may prove to have an added benefit over SIT, since they can be used on an emergency basis.

Furthermore, the testing of either immunoglobulins from SIT patients or the human monoclonals specific for the allergen, e.g. Fel d1, may be tested in any one of the in vitro diagnostic tests or assays described herein, or may be tested directly in the PCA model.

Thus, the present invention provides a method of determining if a patient suffering from an allergy is responsive to therapy with one or more antibodies or antigen binding fragments thereof specific for the allergen, the method comprising:
a) collecting a sample of tissue or an extract thereof, or a biological fluid, or a blood sample from a patient suffering from an allergy;
b) extracting allergen specific IgE from any one or more of the patient samples of (a);
c) mixing the IgE from the patient sample with the allergen and with one or more antibodies or antigen binding fragments thereof specific for the allergen; and
d) determining if the addition of the antibodies or antigen binding fragments thereof specific for the allergen blocks the binding of the allergen specific IgE from step b) to the allergen,
wherein the ability of the one or more antibodies or antigen binding fragments thereof specific for the allergen to block the binding of allergen specific IgE from step b) to the allergen is indicative that the patient suffering from an allergy is responsive to therapy with the one or more antibodies specific for the allergen.

Therapeutic Antibodies for Use in Treating Allergies
Preparation of Human Antibodies Methods for generating human antibodies in transgenic mice are known in the art. Any such known methods can be used in the context of the present invention to make human antibodies that specifically bind to any antigen.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to an allergen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

According to certain embodiments, the antibodies used in the methods of the present invention to confer protection in the PCA model are human monoclonal antibodies that specifically bind Fel d1. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" Fel d1, as used in the context of the present invention, includes antibodies that bind Fel d1 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay.

According to certain exemplary embodiments of the present invention, the Fel d1 monoclonal antibodies, or antigen-binding fragments thereof that can be used in the context of the methods of the present invention comprise the heavy chain complementarity determining regions (HCDRs) of a heavy chain variable region (HCVR) comprising the amino acid sequence of SEQ ID NO: 2 or 18 and the light chain complementarity determining regions (LCDRs) of a light chain variable region (LCVR) comprising the amino acid sequence of SEQ ID NO: 10 or 26. According to certain embodiments, the anti-Fel d1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:4 or 20; the HCDR2 comprises the amino acid sequence of SEQ ID NO:6 or 22; the HCDR3 comprises the amino acid sequence of SEQ ID NO:8 or 24; the LCDR1 comprises the amino acid sequence of SEQ ID NO:12 or 28; the LCDR2 comprises the amino acid sequence of SEQ ID NO:14 or 30; and the LCDR3 comprises the amino acid sequence of SEQ ID NO:16 or 32. In yet other embodiments, the anti-Fel d1 antibody or antigen-binding fragment thereof comprises an HCVR comprising SEQ ID NO:2 or 18 and an LCVR comprising SEQ ID NO:10 or 26. In certain embodiments, the methods of the invention provide for the use of a composition comprising two anti-Fel d1 monoclonal antibodies having the HCVR/LCVR amino acid sequence pairs as set forth in SEQ ID NOs: 2/10 and 18/26.

Pharmaceutical Compositions

The present invention may include methods, which comprise administering an allergen-specific antibody, e.g. a Fel d1 antibody, to a subject wherein the antibody is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in US Patent Application Publication No. 2012/0097565.

Dosage

The amount of Fel d1 antibody administered to a subject according to the methods of the present invention is, generally, a therapeutically effective amount. As used herein, the phrase "therapeutically effective amount" means an amount of the antibody that results in one or more of: (a) a reduction in the severity or duration of an allergic reaction; (b) the alleviation of one or more symptoms or indicia of an allergic reaction; (c) prevention or alleviation of anaphylaxis; (d) a reduction in serum IgE level; (e) a reduction in the use or need for conventional allergy therapy (e.g., reduced or eliminated use of antihistamines, decongestants, nasal or inhaled steroids, anti-IgE treatment, epinephrine, etc.).

In the case of an anti-Fel d1 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 300 mg of an anti-IL-4R antibody is administered.

The amount of Fel d1 antibody contained within the individual doses may be expressed in terms of milligrams of antibody per kilogram of patient body weight (i.e., mg/kg). For example, the antibody may be administered to a patient at a dose of about 0.0001 to about 10 mg/kg of patient body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Blocking Mast Cell Degranulation by Polyclonal Antibodies Generated During Allergen-Specific Immunotherapy Against the Cat Allergen Fel d1 and with Human Monoclonal Antibodies that Specifically Bind Fel d1

The passive cutaneous anaphylaxis (PCA) in vivo model is used to assess in vivo mast cell degranulation. The model relies on the passive transfer of antisera containing allergen-specific mouse polyclonal IgE, which binds to FcεR1 on mast cells near the site of administration. The mice are effectively "sensitized" locally to the specific antigen(s) (either Fel d 1 or peanut as a control) used to generate the antiserum. When antigen is subsequently injected systemically as an allergen challenge along with Evan's blue dye, antigen-induced mast cell degranulation results in rapid capillary dilation and increased vascular permeability that can be visualized and quantitated by measuring dye leakage into the reaction site. In this model, the peanut-sensitized ear provides an internal control for the specificity of the effector cell response when Fel d 1 is injected as the challenge. Mast cell activation has several measurable downstream effects. For instance, mucosal-associated mast cell release of histamine and other molecules stimulates the dilation of blood vessels, irritation of nerve endings and an increase in fluid accumulation. These events cause local swelling, increased mucus production and itching, which together lead to the symptoms characteristic of an ocular allergic response and allergic rhinitis in humans. The PCA model, which measures mast cell-induced vascular permeability, has been used to study hypersensitivity in various settings (Bradley, et al. 1991, J Allergy Clin Immunol; 88:661-74). In particular, the PCA model is a sensitive model that has been used to test the ability of Fel d 1-specific antibodies, both alone and as multi-antibody cocktails, to block mast cell degranulation induced by Fel d 1.

SIT is a disease modifying therapy that introduces a regimen of increasing doses of allergen with the goal of stimulating immune tolerance through repeated exposure, a process that can take years to confer protection. SIT has been shown to induce the production of allergen-specific polyclonal immunoglobulins (IgGs) that, when passively transferred, inhibit immediate inflammatory responses in allergic patients that have not undergone SIT (Cooke, et al, 1935. 62:733-50).

The PCA model can be used to assess the degree to which polyclonal IgG antibodies generated during SIT block mast cell degranulation induced by Fel d 1. The PCA model can also be used to compare the protective effect of SIT-induced polyclonal IgG antibodies to the protective effect of Fel d 1-specific monoclonal antibodies, administered passively as either individual or as multi-antibody cocktails. While the present study describes the results obtained using blood samples obtained from patients undergoing allergen-specific immunotherapy (SIT) for the cat allergen Fel d1, it is feasible that similar results may be observed using samples from patients after undergoing SIT for other allergens. Moreover, the method described herein can be used to determine if a patient has responded to SIT by assessing the amount and/or capability of allergen-specific IgG in a patient sample to prevent mast cell degranulation.

Methods and Results

For generating antisera used in the PCA model, Balb/c mice were sensitized by intraperitoneal injection on day 0 with 5 µg natural Fel d1 protein purified from cat hair extract (Indoor Biotechnologies, #LTN-FD1-1) or with 5 µg of crude peanut allergen extract (Greer Laboratories, #XPF171D3A25) in a solution of 1 mg/ml of alum (Pierce, #77161) in 1× phosphate buffered saline. Two weeks later (day 14) sensitized mice were boosted with doses of allergen identical to those used for the initial immunization. Two weeks after the boost (day 28), mice were sacrificed and serum was collected. Total IgE concentration in the isolated antisera was determined by ELISA. The final concentration of antiserum was diluted to 2500 ng/mL total IgE in 1× phosphate buffered saline.

For generating antibodies to Fel d1, an immunogen comprising any one of the following can be used. In certain embodiments, the antibodies of the invention are obtained from mice immunized with a primary immunogen, such as full length natural Fel d1 (nFel d1), which may be purchased commercially (e.g., from Indoor Biotechnologies, #LTN-FD1-1), or isolated from cat hair or dander by multi-step column chromatography (See, for example, Chapman M D, et al. (1988), J. Immunol. 140:812-818), or which may be produced recombinantly (See GenBank accession numbers P30438, or NP_001041618.1 for the full length amino acid sequence of chain 1 of Fel d1, also referred to as chain A or FELD1 A; also see SEQ ID NO: 33) and GenBank accession number P30440, or NP_001041619.1 for the full length amino acid sequence of chain 2 of Fel d1 (also referred to as chain B or FELD B; also see SEQ ID NO: 34), or fragments of either chain 1 or chain 2, or fragments from both chain 1 and chain 2 of the Fel d1 protein, followed by immunization with a secondary immunogen, or with an immunogenically active fragment of the natural protein. Animals may be immunized with either chain 1 protein alone or chain 2 protein alone, or with both chain 1 and chain 2 proteins, administered sequentially, or concurrently. Various constructs may be prepared using portions of chain 1 and chain 2 along with various linking or spacer strategies known to those skilled in the art. These constructs may be used alone, or in various combinations to elicit antibody responses in vivo.

Fully human Fel d 1-specific monoclonal antibodies H4H1232N, H4H2636P and H4H1238 were generated as described herein (See also U.S. Ser. No. 13/875,401) and the amino acid sequences of the heavy chain and light chain variable regions and their respective heavy chain and light chain complementary determining regions are included herein and are shown in Table 1 below.

TABLE 1

| Ab Protein Identification No. | Amino Acid SEQ ID NOs | | | | | | | |
|---|---|---|---|---|---|---|---|---|
| | HCVR | HCDR1 | HCDR2 | HCDR3 | LCVR | LCDR1 | LCDR2 | LCDR3 |
| H4H1232N | 2 | 4 | 6 | 8 | 10 | 12 | 14 | 16 |
| H4H2636P | 18 | 20 | 22 | 24 | 26 | 28 | 30 | 32 |
| H4H1238N | 36 | 38 | 40 | 42 | 44 | 46 | 48 | 50 |

Sera were collected from cat allergic patients who had either undergone or not undergone specific immunotherapy for cat allergy. The concentration of total IgG (and therefore of Fel d 1-specific IgG) contained in these samples was then increased to support administration in vivo in the PCA model. This was achieved by isolation of total IgG using protein G affinity resin, dialysis of the eluted IgG into PBS, and then concentration of the total IgG using a molecular weight cut-off membrane. Total and Fel d 1-specific IgG levels were quantitated in sera samples and purified IgG from cat allergic patients using an ELISA. Microtiter plates were coated with 2 µg/mL of either natural Fel d 1 (LoTox nFel d 1, #LTN-FD1) or anti-human IgG (Jackson Immunoresearch, #109-005-098) in phosphate-buffered saline (PBS) overnight at 4° C. The plates were blocked with 0.5% bovine serum albumin (BSA). Sera or purified IgG were serially diluted in 0.5% BSA-PBS and added to the plates and incubated for 1 hour at RT. For total IgG quantitation, a standard curve was generated using human IgG (Thermo Scientific, #31154), while for Fel d 1-specific IgG quantitation, a standard curve was generated using a Fel d 1 human kappa monoclonal antibody (H4H1238N). Goat anti-human IgG-Fc-Horse Radish Peroxidase (HRP) conjugated secondary antibody (Jackson Immunoresearch, Catalogue No. 109-035-098) was added (1:5000 dilution), followed by addition of TMB/$H_2O_2$ substrate to detect IgG. Concentrations of total and Fel d 1 specific IgG were computed from the respective standard curve plots and are shown in Table 2.

TABLE 2

Characterization of Sera Obtained from Cat Allergic Patients

| Sample Name | Immunotherapy | SIT Duration (months) | Total Human IgG in Sera (mg/ml) | Purified and concentrated IgG (mg/ml) | Total Fel d 1-specific IgG in Sera (mg/ml) | Total Fel d 1-specific IgG in Purified and concentrated Sera (mg/ml) |
|---|---|---|---|---|---|---|
| AMC-003 | NO | 0 | 14.7 | 107 | Not detectable | 0.008 |
| AMC-004 | NO | 0 | 11.1 | 112 | Not detectable | 0.007 |
| AMC-005 | YES | 14 | 18.1 | 131 | 0.014 | 0.059 |
| AMC-007 | YES | 20 | 14.8 | 146 | 0.013 | 0.119 |
| AMC-010 | YES | 37 | 15.8 | 161 | 0.050 | 0.463 |
| AMC-001 | NO | 0 | 12.6 | 61.7 | 0.005 | 0.025 |
| AMC-002 | YES | 27 | 8.9 | 61.7 | 0.013 | 0.078 |
| AMC-006 | NO | 0 | 13.7 | 60.6 | Not detectable | 0.010 |
| AMC-008 | YES | 20 | 13.1 | 67.1 | Not detectable | 0.015 |
| AMC-009 | NO | 0 | 10.4 | 62.7 | Not detectable | 0.015 |

The concentration of Fel d 1-specific IgG was highest in a serum sample from the patient who had undergone SIT for the longest duration (sample AMC-010 exhibited serum levels of 0.050 mg/mL after SIT treatment spanning 37 months). For sera from cat allergic patients who did not undergo SIT (see patients AMC-003, AMC-004, AMC-001, AMC-006 and AMC-009), Fel d 1-specific IgG levels were either 0.005 mg/ml or below the detection limit in initial sera but could be measured after the protein G isolation and concentration procedure. For the four sera samples from patients subjected to SIT with measurable Fel d 1 specific IgG in the initial sera (AMC-005, AMC-007, AMC-010, AMC-002), the protein G isolation and concentration procedure resulted in increasing the Fel d 1-specific IgG concentrations by factors of 4.2, 9.2, 9.3, and 6.0 respectively, relative to the concentration in the initial serum (calculated based on the numbers in Table 2).

To evaluate the protective effect in the PCA model from administration of the patient-derived IgG and from a cocktail of two Fel d 1-specific antibodies that do not cross-compete for binding to Fel d 1 (See US2013/0295097), groups of Balb/c mice were injected subcutaneously with either of four different treatments: i) a human IgG4 isotype control antibody, ii) a combination of Fel d 1-specific antibodies H4H1232N/H4H2636P, iii) IgG isolated from cat allergic patients (AMC-003 and AMC-004) who had not undergone SIT, or iv) IgG isolated from cat allergic patients (AMC-005, AMC-007 and AMC-010) who had undergone SIT for cat allergy. The IgG4 isotype control antibody and the combination of two Fel d 1 antibodies were injected subcutaneously at doses of 1 mg/kg total antibody (0.5 mg/kg of each antibody for the H4H1232N/H4H2636P combination treatment). The isolated and concentrated IgG samples from cat allergic patients (either with or without SIT therapy) were injected at volumes approximately one-tenth the blood volume of the mice used in these studies (i.e., 200 uL volumes were injected, and the expected blood volume is approximately 2.0 mL for a 20 g mouse). Given the concentration factors described above for the SIT patient serum samples, this dosing procedure was expected to reconstitute approximately 42%, 92%, and 93%, respectively, of the original serum levels of Fel d 1-specific IgG for samples AMC-005, AMC-007, and AMC-010, respectively. Three days after pre-treatment with antibodies, mice were sensitized by intradermal injection with 10 µl of natural Fel d 1-derived antiserum or 10 µl of peanut-derived antiserum (negative control) into the right and left ears, respectively, of each mouse. Twenty-four hours after sensitization, mice were challenged by intravenous injection (100 µL per mouse) of a solution of 1 µg/mL natural Fel d 1 (Indoor Biotechnologies, #LTN-FD1-1) dissolved in 1× phosphate buffered saline containing 0.5% (w/v) Evan's blue dye (Sigma, #E2129). One hour after antigen challenge, mice were sacrificed, ears were excised and placed in 1 mL formamide and incubated for 3 days at 56° C. to extract the Evan's blue dye from the tissue. Ear tissue was then removed from the formamide, blotted to remove excess liquid and weighed. Two hundred microliter aliquots of each formamide extract were transferred to 96 well plates in duplicate. Absorbance of the resulting supernatants was measured at 620 nm. The OD was converted to Evan's blue dye concentration using a standard curve. The average concentration of Evan's blue dye extravasated into the tissue of the antisera-sensitized ear (normalized by ear tissue weight) was calculated for the group treated with the isotype control antibody and defined as F(isotype,avg). The reduction in Evan's blue dye extravasation resulting from antibody pre-treatment was calculated per mouse by subtracting the amount of Evan's blue dye for the antibody-treated group's Fel d 1 extract sensitized ear, defined as F(mAb,i), from F(isotype,avg). This number was then divided by the difference between F(isotype,avg) and the dye amount for the antibody-treated group's peanut sensitized ear [P(mAb, i)] and multiplied by 100 to give the overall percent reduction in dye extravasation for each mouse (% Reduction).

$$\% \text{ Reduction (per mouse)} = 100 * [F(\text{isotype,avg}) - F(mAb,i)] / [F(\text{isotype,avg}) - P(mAb,i)]$$

The average percent reduction in dye leakage was then calculated for each group. Results, expressed as (mean±SEM) of percent Evan's blue reduction are shown in Table 3. All reductions that were statistically significant ($p<0.05$) compared to isotype control as determined by two-way ANOVA with Bonferroni's post-test are noted with an asterisk (*). The number of mice used per group (n) is noted within parentheses in the tables.

TABLE 3

Percent reduction in dye extravasation in the PCA model

| Treatment | % Reduction in Dye Extravasation (±SEM) |
|---|---|
| H4H1232N/H4H2636P (n = 10) | 63 ± 4* |
| AMC-005 (SIT IgG) (n = 9) | 20 ± 4 |
| AMC-007 (SIT IgG) (n = 10) | 50 ± 5* |
| AMC-010 (SIT IgG) (n = 10) | 67 ± 4* |
| AMC-003 (non-SIT IgG) (n = 10) | 13 ± 2 |
| AMC-004 (non-SIT IgG) (n = 10) | 5 ± 6 |

As shown in Table 3, groups of mice when treated with the Fel d 1 antibody cocktail H4H1232N/H4H2636P exhibit a 63% reduction in dye extravasation compared to mice receiving control antibody. Mice treated with cat allergic sera from patients who underwent SIT exhibit 20% (AMC-005), 50% (AMC-007) and 67% (AMC-010) reductions in dye extravasation compared to mice receiving isotype control antibody demonstrating that purified IgG from cat allergic patients who underwent SIT are efficacious in this model. The percent reduction in dye extravasation correlates with the duration of SIT therapy and also the amount of Fel d 1 specific IgG present in the sera (Table 2). Mice treated with cat allergic sera from patients who did not undergo SIT exhibited 13% (AMC-003) and 5% (AMC-004) reductions in dye extravasation compared to mice receiving control antibody, which did not achieve statistical significance in this study compared to treatment with isotype control.

As shown in Table 3 the H4H1232N/H4H2636P antibody cocktail at its dose of 1 mg/kg (0.5 mg/kg each mAb) achieved similar potency (63±4% reduction in dye extravasation) as treatment with the SIT patient-derived sample with the highest Fel d 1-specific IgG concentration (sample AMC-010; 67±4% reduction in dye extravasation). The approximate dosing level for AMC-010 can be estimated as ~4.6 mg/kg since 0.093 mg of Fel d 1-specific IgG was injected per mouse (200 uL per injection*0.46 mg/mL of Fel d 1-specific IgG in this sample), and the approximate weight per mouse was 0.020 kg. This demonstrates that the H4H1232N/H4H2636P treatment was about 5-fold more potent than the SIT patient derived Fel d 1-specific IgG based on total antibody mass dosage.

Example 2

Peanut Specific Antibodies Generated Through Allergen Specific Immunotherapy Block Mast Cell Degranulation in a Mouse Peanut Allergy Model Methods/Experimental Design A mouse peanut specific immunotherapy model was developed based in part on the model delineated in Kulis et al., *J. Allergy Clin Immunol.* 127(1):81-88(2011). An outline of the experimental protocol is shown in FIG. 1a. Two groups of mice were used in these experiments. One group (SIT') was subjected to a peanut specific immunotherapy regimen comprising a Sensitization Phase, a Build-up Phase, and a Challenge. The Sensitization Phase consisted of administration of 0.5 mg peanut extract (Greer laboratories, Part Number XPF171D3A25)+2 mg Alum administered intraperitoneally on Days 0, 7 and 28. The Build-up Phase consisted of twelve separate intraperitoneal administrations of various increasing doses of peanut extract shown in FIG. 1a without Alum on Days 49, 51, 53, 56, 58, 60, 63, 65, 67, 70, 72 and 74. The Challenge consisted of intraperitoneal administration of 1 mg of peanut extract on Day 98. The other group of mice (No SIT') was subjected to a Sensitization phase and a challenge phase.

To assess the extent of anaphylaxis in this system and the efficacy of the specific immunotherapy, mouse core temperature was measured over the course of 180 minutes following the challenge injection. A decrease in core temperature is a measure of anaphylaxis. Mice subjected to the peanut specific immunotherapy regimen were protected from the peanut induced decrease in core temperature (FIG. 1B). Sera from these mice that had either undergone or not undergone peanut specific immunotherapy were collected at the completion of the experiment (day 98) for immunoglobulin measurements. Total IgE, peanut-specific IgG1 and peanut specific IgG2a at day 96 are shown in Table 4. Total IgE was determined in the samples using a mouse IgE ELISA kit (BD OpT EIA, #555248) according to the manufacturers instructions. Peanut specific IgG1 and peanut specific IgG2a were determined by sandwich ELISAs using coated peanut extract as the capture surface and anti-mouse IgG2 antibody (HRP-rat anti-mouse IgG2a from BD biosciences, Cat. No. 553391) or anti-mouse IgG1 antibody (HRP-rat anti-mouse IgG1 from BD biosciences, Cat. No. 559626) for detection. Total IgE, peanut specific IgG1 and peanut IgG2a levels are higher in serum samples from mice that received SIT (Table 4).

To evaluate the protective effect of SIT, the PCA model was conducted in groups of Balb/c mice that were subcutaneously administered 200 µl of either PBS, sera from mice that received SIT or sera from mice that were sensitized and did not receive SIT. Three days after the treatment with sera, mice were sensitized by either intradermal injection with 10 µl of peanut-extract-derived antiserum or 10 µl of Fel d 1 derived antiserum (negative control) into the right and left ears, respectively, of each mouse. Twenty-four hours after sensitization, mice were challenged by intravenous injection (100 µl per mouse) of a solution comprised of 250 µg of peanut extract dissolved in 1×PBS containing 0.5% Evans blue dye (Sigma, #E2129).

One hour after antigen challenge, mice were sacrificed, ears were excised and placed in 1 mL formamide and incubated for 3 days at 56° C. to extract the Evans blue dye from the tissue. Ear tissue was then removed from the formamide, blotted to remove excess liquid and weighed. Two hundred microliter aliquots of each formamide extract were transferred to 96 well plates in duplicate. Fluorescence of the resulting supernatants was measured using an excitation measurement of 625 nm and emission measurement of 680 nm. The fluorescence was converted to Evans blue dye concentration using a standard curve. The average concentration of Evans blue dye extravasated into the tissue of the antisera-sensitized ear (normalized by ear tissue weight) was calculated for the group treated with Control PBS treated and defined as F(control,avg). The reduction in Evans blue dye extravasation resulting from antibody pre-treatment was calculated per mouse by subtracting the amount of Evans blue dye for the Sera-treated group's peanut extract sensitized ear, defined as F(sera,i), from F(control,avg). This number was then divided by the difference between F(control,avg) and the dye amount for the antibody-treated group's peanut sensitized ear [P(sera,i)] and multiplied by 100 to give the overall percent reduction in dye extravasation for each mouse (% Reduction).

The average percent reduction in dye leakage was then calculated for each group. Results, expressed as (mean±SD) of percent Evans blue reduction are shown in Table 5. All reductions that were statistically significant (p<0.05) compared to isotype control as determined by two-way ANOVA with Bonferroni's post-test are noted with an asterisk (*). The number of mice used per group (n) is noted within parentheses in the tables.

Results

As shown in table 5, groups of mice when treated with peanut SIT antisera exhibit a 97% reduction in dye extravasation compared to mice that received PBS alone. The percent reduction in dye extravasation correlates with peanut specific IgG present in the sera, demonstrating the protective effects of peanut specific IgG that is present in the SIT antisera in this model.

TABLE 4

Characterization of sera obtained from mice in a peanut specific immunotherapy model

| | No SIT (n = 5) | SIT (n = 4) |
|---|---|---|
| Total IgE (ng/mL) | 1656 | 7896 |
| Peanut specific IgG1 (titer) | 60596 | 8287003 |
| Peanut specific IgG2a (titer) | 764 | 26821 |

TABLE 5

Percent reduction in dye extravasation in the PCA model

| Treatment | % Reduction in Dye extravasation (±SD) as compared with PBS control |
|---|---|
| No SIT (n = 5) | 0 |
| SIT (n = 5) | 97 ± 5 |

Example 3

An In Vitro Assay/Method to Assess the Ability of Antibodies to Block the Binding of Allergen-Specific Polyclonal IgE to Allergen Below is described an assay to evaluate the blockade of Fel d 1 binding to cat allergic human IgE by Fel d 1-specific IgGs isolated from subjects treated by allergen specific immunotherapy (SIT).

Blocking Fel d 1 Binding to Allergen Specific IgE by Antibodies Isolated from Patients Undergoing SIT The ability of IgG antibodies from a cat allergic SIT patient serum to block Fel d 1 binding to plate-captured IgE from cat allergic human donor plasma/sera was determined using a blocking ELISA. Microtiter plates were coated overnight at 4° C. with a human FcεR1a (the high affinity receptor for IgE) extracellular domain protein that was produced with a C-terminal mouse Fc tag (hFcεR1α-mFc; SEQ ID NO: 51). Plates were blocked with 0.5% BSA (w/v) for 1 hour at room temperature (RT). Plasma from Fel d 1 cat positive allergic donors (Plasma Lab International, Everett, Wash.) was diluted 5-fold and total IgE was captured over the receptor-coated surface. A constant amount of recombinant Fel d 1 produced with a C-terminal myc-mychexahistidine tag (Fel d 1-mmH; SEQ ID NO: 52) (0.7 nM) was pre-mixed with serial dilutions of Fel d 1 antibodies (isolated by protein G affinity purification from sera from human patients undergoing cat allergen specific immunotherapy) ranging from 66.67 nM to 1.13 pM and incubated for 1 hour at RT. The antibody-Fel d 1 mixture was then added to the IgE-coated plate for 1 hour. Plates were subsequently washed and the amount of free Fel d 1-mmH bound to plate was detected using an anti-myc antibody derived from clone 9E10 (Evan G I, et al. Isolation of monoclonal antibodies specific for human c-myc proto-oncogene product. Mol. Cell. Biol. 5: 3610-3616, 1985) that was produced in-house as a human IgG1 isotype, conjugated to HRP, and incubated at a final concentration of 0.102 ug/mL for 1 hour at RT. Plates were washed with PBS-T in between each step of the ELISA protocol described above. To develop the colorimetric reaction, TMB/$H_2O_2$ substrate was added to the plates and incubated for 20 minutes at RT. The reaction was stopped using 2N sulfuric acid ($H_2SO_4$; VWR, #BDH3500-1). Absorbance was subsequently measured on a spectrophotometer (Victor, Perkin Elmer) at 450 nm. The concentration of antibody required to inhibit the signal of a constant concentration of Fel d 1 by 50% ($IC_{50}$) was determined using Prism software (data not shown).

Figure 2:
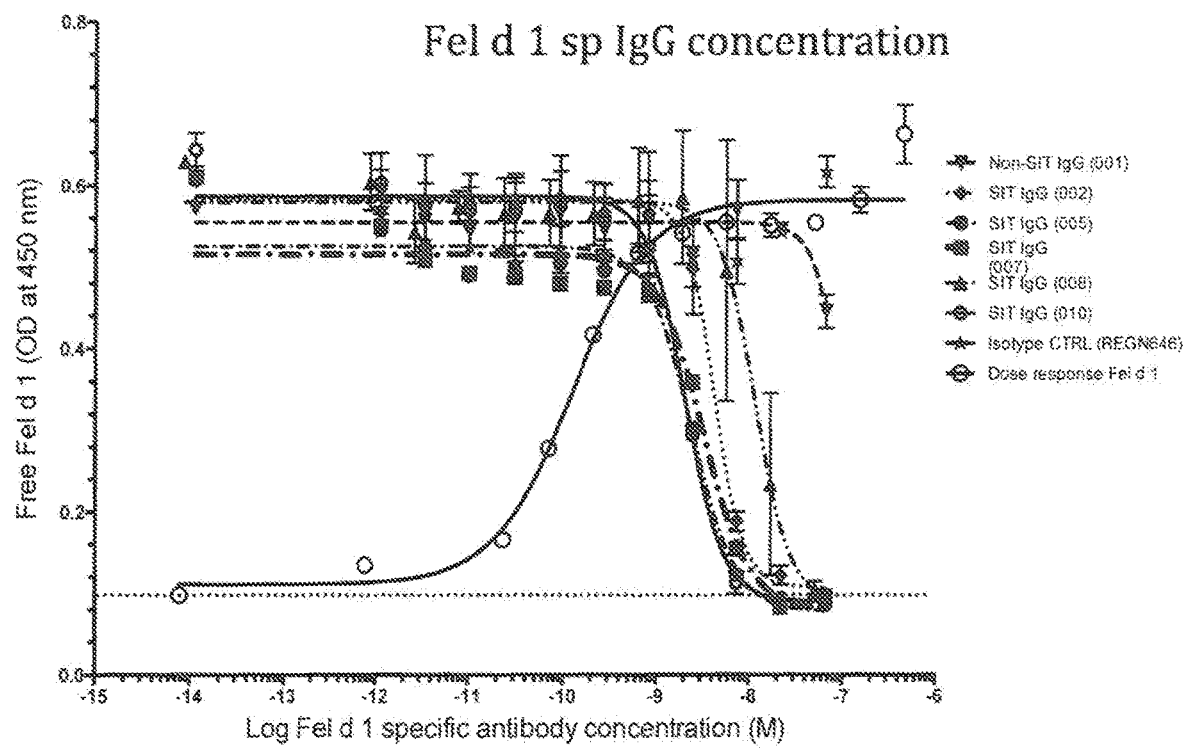
FIG. 2. Shows the results of a blocking assay for Fel d 1 binding to allergic IgE (donor 1) by anti-Fel d 1 IgG elicited by SIT.
Figure 3:
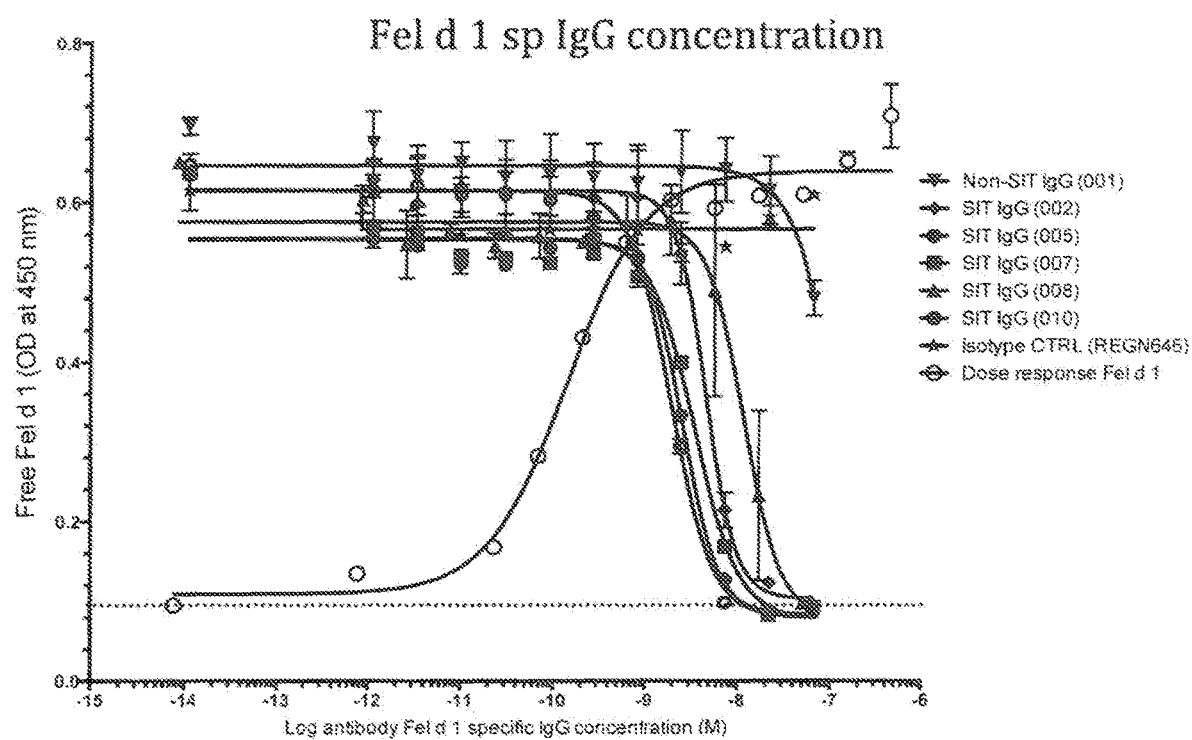
FIG. 3. Shows the results of a blocking assay for Fel d 1 binding to allergic IgE (donor 2) by anti-Fel d 1 IgG elicited by SIT.

Representative results from the blocking assay are shown in FIGS. 2-3 for two different cat allergic human donor IgE samples. Purified IgG isolated from patients undergoing SIT with detectable levels of Fel d 1 specific IgG blocked Fel d 1 binding to FcεR1α-captured allergic IgE to the assay baseline (complete blocking), while an irrelevant control antibody did not block. Similar complete blocking in this assay was observed for SIT IgG from 4 additional allergic donors that were tested. When sera from patients undergoing SIT were collected at different time points (once in 2013 and once in 2014), the blocking activity was maintained (data not shown). IgG from a patient not undergoing SIT exhibited a low degree of blocking, but only at the highest antibody concentration tested in the assay (FIGS. 2-3, non SIT IgG). This may be attributable to the low, but detectable, levels of Fel d 1 specific IgG in this sample (See Table 2).

Figure 4:
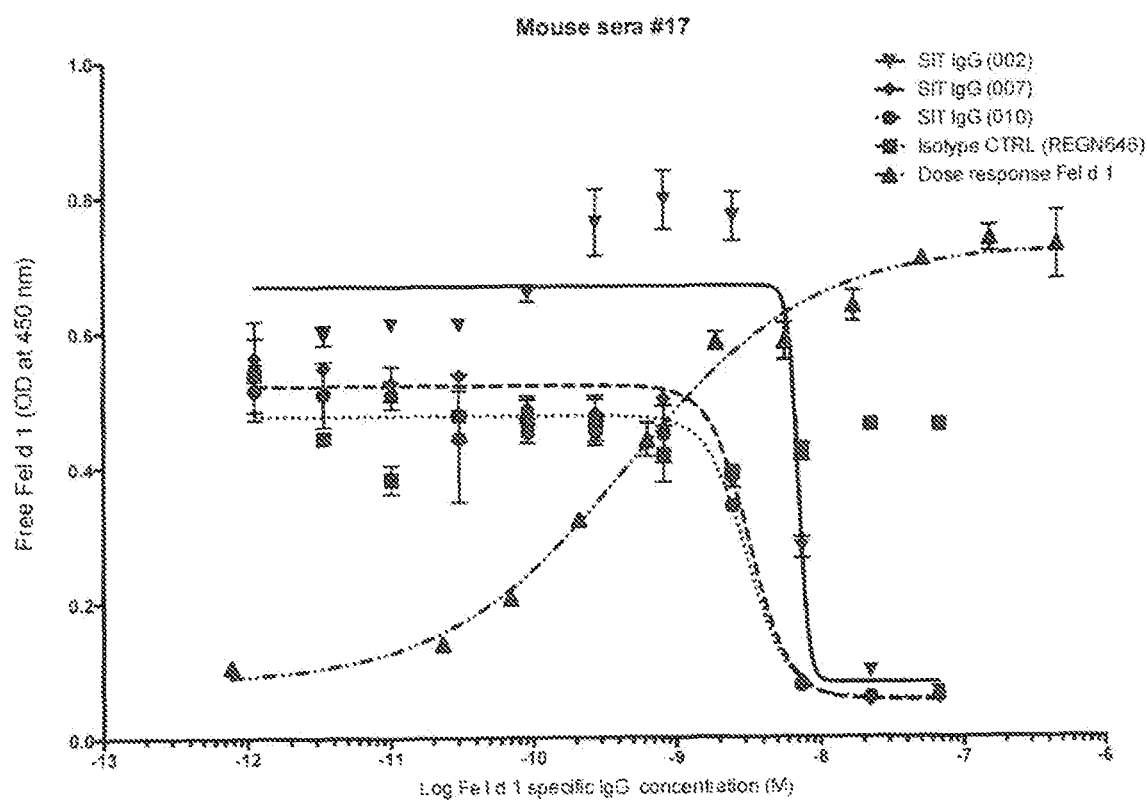
FIG. 4. Shows the results of a blocking assay for Fel d 1 binding to allergic IgE (mouse sera immunized with Fel d 1) by anti-Fel d 1 IgG elicited by SIT.

Similar results as described above and in FIG. 2 using captured Fel d 1 allergic human IgE were also observed using captured polyclonal mouse IgE obtained from the sera of mice immunized with Fel d 1 protein. The capture surface was effective in this assay because human FcεR1a binds to mouse IgE. The ability of Fel d 1-specific IgG isolated from three different human SIT sera samples to block the binding of Fel d1-mmH to captured mouse IgE from Fel d 1-immunized mice is shown in FIG. 4.

Example 4

Blocking Fel d 1 Binding to Allergen Specific IgE by Anti-Fel d 1 Polyclonal Serum from Mice Immunized with Fel d 1

Figure 5:
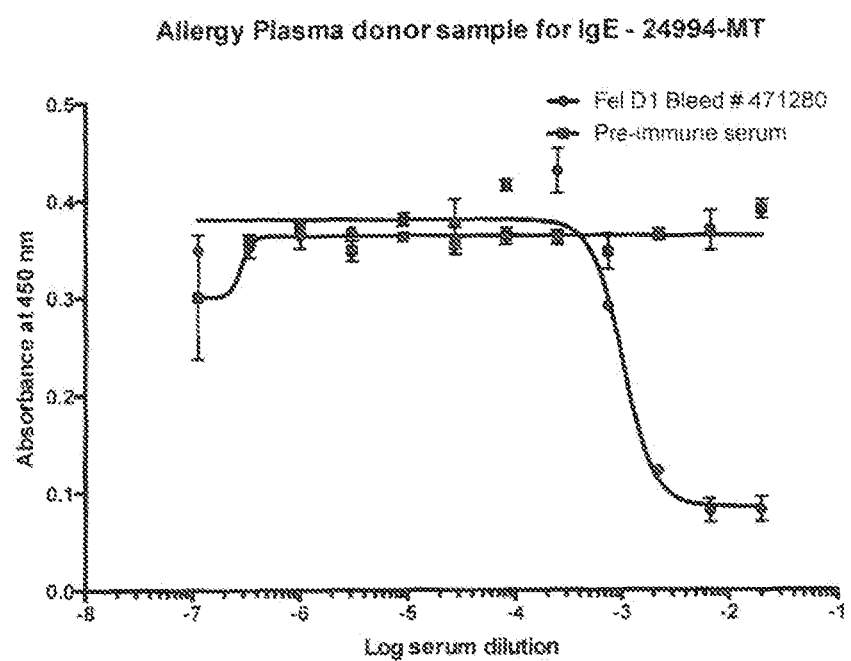
FIG. 5. Shows the results of a blocking assay for Fel d 1 binding to human allergic IgE by anti-Fel d 1 mouse sera elicited by immunization with Fel d 1.

Polyclonal serum from a mouse immunized with Fel d 1 mFc (REGN573; SEQ ID NO: 53) was used as a source of Fel d 1 specific IgG to mimic the IgG from allergy patients undergoing immunotherapy in the blocking assay described above. The immune mouse serum was serially diluted starting from 1:50 and diluted 3-fold. The immune serum blocked Fel d 1 binding to FcεR1α-captured allergy IgE to the assay baseline, while pooled pre-immune sera did not block (FIG. 5).

What is claimed is:

1. A method for determining the safety or efficacy of an allergen-specific immunotherapy (SIT) in a patient, the method comprising:

(a) quantitating total IgG and allergen-specific IgG from a tissue sample or an extract thereof, a biological fluid, or a blood sample from the patient undergoing SIT;

(b) concentrating total IgG, which includes allergen-specific IgG, from the sample in step (a) from the patient undergoing SIT;

(c) reacting the allergen-specific IgG in the total IgG from step (b) with allergen-specific IgE and the allergen for which the patient is undergoing SIT; and (d) measuring the amount of allergen-specific IgG from step (c) that is bound to the allergen using an in vivo allergen-specific non-human animal model of passive cutaneous anaphylaxis (PCA), where the amount of allergen-specific IgG bound to the allergen is measured by at least a 30% reduction in dye extravasation when compared to measured dye extravasation in the in vivo allergen-specific non-human animal model of passive cutaneous anaphylaxis (PCA) using concentrated allergen-specific IgG from an allergic patient who has not undergone SIT, and is directly proportional to an increase in the safety or efficacy of allergen-specific immunotherapy (SIT) in a patient.

2. The method of claim 1, where step (a) is performed using an in vitro method selected from the group consisting of an enzyme-linked immunosorbent assay (ELISA), a radioimmunoassay (MA), an immunoradiometric assay (IR-MA), a luminescence immunoassay (LIA), an immunoblot, FACs analysis, an IgE-facilitated allergen binding (GAB) assay, and an assay using an engineered cell line expressing FcεR1.

3. The method of claim 1, wherein the tissue sample is any tissue sample, or extract thereof, biological fluid, or blood sample containing immunoglobulin expressing cells; or the blood sample is selected from the group consisting of whole blood, serum and plasma.

4. The method of claim 1 or 2, wherein the allergen is selected from the group consisting of a food allergen, allergen Fel d1, allergen can f1, allergen can f2, allergen can f3, allergen can f4, allergen can f5, allergen can f6, allergen Betv 1, allergen Cryj1, and allergen Cryj2.

5. The method of claim 1 or 2, wherein the allergen is Fel d1.

\* \* \* \* \*